US008883519B1

(12) United States Patent
Perez et al.

(10) Patent No.: US 8,883,519 B1
(45) Date of Patent: Nov. 11, 2014

(54) OXIDASE ACTIVITY OF POLYMERIC COATED CERIUM OXIDE NANOPARTICLES

(75) Inventors: J. Manuel Perez, Orlando, FL (US); Atul Asati, Orlando, FL (US); Santimukul Santra, Orlando, FL (US); Charalambos Kaittanis, Oviedo, FL (US); Sudip Nath, Iowa City, IA (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 807 days.

(21) Appl. No.: 12/704,678

(22) Filed: Feb. 12, 2010

Related U.S. Application Data

(60) Provisional application No. 61/160,744, filed on Mar. 17, 2009.

(51) Int. Cl.
*G01N 33/553* (2006.01)
*G01N 33/543* (2006.01)

(52) U.S. Cl.
USPC .......................................... 436/525; 436/518

(58) Field of Classification Search
CPC ................ C04B 2235/3229; A61K 2800/413; A61K 49/0423; G03G 9/1075; G03G 9/1139
USPC ................................................. 436/525, 518
See application file for complete search history.

(56) References Cited

U.S. PATENT DOCUMENTS

| 5,089,860 A | 2/1992 | Deppe et al. |
| 5,411,647 A | 5/1995 | Johnson et al. |
| 5,486,359 A | 1/1996 | Caplan et al. |
| 5,910,311 A | 6/1999 | Boussourira |
| 5,961,993 A | 10/1999 | Boussourira |

(Continued)

FOREIGN PATENT DOCUMENTS

| WO | WO 99/15891 | 4/1999 |
| WO | WO 2003/059263 A2 | 7/2003 |

(Continued)

OTHER PUBLICATIONS

Rzigalinski, et al. Cerium oxide nanoparticles increase the lifespan of cultured brain cells and protect against free radical and mechanical trauma, FASEB Journal, 2003, pp. A606, vol. 17, No. 4-5, Abstract No. 3377.24.

(Continued)

*Primary Examiner* — Bao Thuy L Nguyen
*Assistant Examiner* — Pensee Do
(74) *Attorney, Agent, or Firm* — Brian S. Steinberger; Law Offices of Brian S. Steinberger, P.A.

(57) ABSTRACT

Methods, systems, compositions include biocompatible polymer coated nanoceria that function as aqueous redox catalyst with enhanced activity at an acidic to moderately alkaline pH value between 1 and 8. The compositions are used as oxidizing agents for decomposition, decontamination or inactivation of organic contaminants, such as, pesticides and chemical warfare agents. Another use includes nanoceria as targetable nanocatalyst prepared by conjugating various targeting ligands to the nanoparticle coating to form a colorimetric or fluorescent probe in immunoassays and other molecule binding assays that involve the use of a molecule in solution that changes the color of the solution or emits a fluorescent signal, where localization of nanoceria to organs or tissue is assessed by treatment with an oxidation sensitive dye or other detection devices. Versatility and uses of the nanoceria compositions are controlled by pH value, choice of dye substrate and thickness of the polymer coating on the ceria nanoparticles.

38 Claims, 29 Drawing Sheets

(56) References Cited

U.S. PATENT DOCUMENTS

| | | | |
|---|---|---|---|
| 6,042,714 A | 3/2000 | Lin et al. |
| 6,103,247 A | 8/2000 | Boussourira |
| 6,139,985 A | 10/2000 | Borglum et al. |
| 6,316,012 B1 | 11/2001 | N'Guyen |
| 6,327,074 B1 | 12/2001 | Bass et al. |
| 6,368,577 B1 | 4/2002 | Kropf et al. |
| 6,406,685 B1 | 6/2002 | Philippe |
| 6,468,551 B1 | 10/2002 | Diec |
| 6,497,863 B1 | 12/2002 | Wachter |
| 6,497,865 B1 | 12/2002 | Griesbach |
| 6,501,590 B2 | 12/2002 | Bass et al. |
| 6,592,746 B1 | 7/2003 | Schmid-Schoenbein et al. |
| 6,654,161 B2 | 11/2003 | Bass et al. |
| 6,844,387 B2 | 1/2005 | Bass et al. |
| 6,890,896 B1 | 5/2005 | Shashoua |
| 7,005,504 B2 | 2/2006 | Hsei et al. |
| 7,075,707 B1 | 7/2006 | Rapaport et al. |
| 7,141,227 B2 | 11/2006 | Chan |
| 7,270,813 B2 | 9/2007 | Shimp et al. |
| 7,347,987 B2 | 3/2008 | McGinnis et al. |
| 7,431,758 B2 | 10/2008 | Ota et al. |
| 7,442,686 B2 | 10/2008 | Lasko et al. |
| 7,471,706 B2 | 12/2008 | Bass et al. |
| 7,504,356 B1 | 3/2009 | Self et al. |
| 7,507,480 B2 | 3/2009 | Sugama |
| 7,534,453 B1 | 5/2009 | Zigaliznski |
| 7,563,459 B2 | 7/2009 | Phillips et al. |
| 7,642,250 B2 | 1/2010 | Williams |
| 7,687,505 B2 | 3/2010 | Sugaya |
| 7,725,802 B2 | 5/2010 | Eroz et al. |
| 7,772,375 B2 | 8/2010 | Greferath et al. |
| 7,888,119 B2 | 2/2011 | Sugaya et al. |
| 7,899,093 B1 | 3/2011 | Bass et al. |
| 7,906,147 B2 | 3/2011 | Hainfield et al. |
| 7,914,617 B2 | 3/2011 | Yadav |
| 8,080,420 B2 | 12/2011 | Sugaya |
| 8,097,270 B2 | 1/2012 | Ketelson et al. |
| 8,172,901 B2 | 5/2012 | Altman et al. |
| 8,333,993 B1 * | 12/2012 | Perez et al. | 424/489 |
| 2003/0050709 A1 | 3/2003 | Noth et al. |
| 2003/0187077 A1 | 10/2003 | Chane-Ching |
| 2004/0062753 A1 | 4/2004 | Rezania et al. |
| 2005/0159820 A1 | 7/2005 | Yoshikawa et al. |
| 2005/0164377 A1 | 7/2005 | Miyabayashi et al. |
| 2005/0171192 A1 | 8/2005 | Gehlsen |
| 2006/0014938 A1 * | 1/2006 | Groman et al. | 534/15 |
| 2006/0110440 A1 | 5/2006 | Sugaya |
| 2006/0280729 A1 | 12/2006 | Mistry |
| 2007/0003621 A1 | 1/2007 | Nangia et al. |
| 2009/0087493 A1 | 4/2009 | Dai et al. |
| 2009/0098574 A1 | 4/2009 | Brisson et al. |
| 2010/0151000 A1 | 6/2010 | Thomas et al. |

FOREIGN PATENT DOCUMENTS

| | | |
|---|---|---|
| WO | WO 2006/118954 | 11/2006 |
| WO | WO 2006/118954 A2 | 11/2006 |
| WO | WO 2007/002662 | 1/2007 |
| WO | WO 2007/002662 A2 | 1/2007 |
| WO | WO 2008/064357 A2 | 5/2008 |
| WO | PCT/US2009/041675 | 6/2009 |
| WO | WO 2009/132277 A1 | 10/2009 |

OTHER PUBLICATIONS

Niu, et al., Cardioprotective effects of cerium oxide nanoparticles in a transgenic murine model of cardiomyopathy, Cardiovas. Res., 2006, pp. 549-559, vol. 73, No. 3.

Qureshi, et al. Increased exhaled nitric oxide following autologous peripheral hemotopietic stem-cell transplantation: a potential marker of idopathic pneumonia syndrome, Chest, 2004, pp. 281-287, vol. 125, No. 1.

Ohgushi, et al., Stem cell technology and bioceramics: from cell to gene engineering, J. Biomed. Mat. Res., 1999, pp. 913-927, vol. 48, abstract.

Dal Maschio, et al., Influence of Ce3+/Ce4+ ratio on phase stability and residual stress field in ceria-yttria stabilized zirconia plasma-sprayed coatings, J. Mat. Sci., 1992, pp. 5591-5596, vol. 27, abstract.

Ramsfjell, et al., Distinct requirements for optimal growth and in vitro expansion of human CD34+ CD38– bone marrow long-term culture-initiating cells (LTC-IC), extended LTC-IC, and murine in vivo long-term reconstituting stem cells, Blood, 1999, pp. 4093-4102, vol. 99, No. 12, abstract.

Devasenpathi, et al., Forming near net shape free-standing components by plasma spraying, Mat. Let., 2002, pp. 882-886, vol. 57.

Imamura, et al., Drusen, choroidal neovascularization, and retinal pigment epithelium dysfunction in SOD1– deficient mice: a model of age-related macular degeneration, PNAS, 2006, pp. 11282-11287, vol. 103, No. 30.

Hollyfield, et al., Oxidative damage-induced inflammation initiates age-related macular degeneration, Nature Medicine, 2008, pp. 194-198, vol. 14.

Birch, et al., Age-related macular degeneration: a target for nanotechnology derived medicines, International Journal of Nanomedicine, 2007, pp. 65-77, vol. 2, No. 1.

Maulik, N., Reactive oxygen species drives myocardial angiogenesis?, Antioxidants & Redox Signaling, 2006, pp. 2161-2168, vol. 8, Nos. 11-12.

McGinnis, et al. U.S. Appl. No. 12/772,523 Office Action mailed Sep. 15, 2011.

Ohia, et al., Pharmacological consequences of oxidative stress in ocular tissues, Mutation Research, 2005, pp. 22-36, vol. 579.

Liu, et al. Subtype lesions of neovascular age-related macular degeneration in Chinese patients, Braefe's Arch Clin Exp Opthalmol, 2007, pp. 1441-1445, vol. 245.

Silva, Seeing the benefits of ceria, Nature Nanotechnology, 2006, pp. 92-94, vol. 1.

Hahn, et al., Maculas affected by age-related macular degeneration contain increased chelatable iron in the retinal pigment epithelium and Bruch's membrane, Arch. Opthalmol., 2003, pp. 1099-1105, vol. 121.

Haywood, et al., Inflammation and angiogenesis in osteoarthritis, Arthritis & Rheumatism, 2003, pp. 2173-2177, vol. 48, No. 8.

Chen, et al., Rare earth nanoparticles prevent retinal degeneration induced by intracellular peroxides, Nature Nano Technology, 2006, pp. 142-148, vol. 1, No. 2, abstract.

Moongkarndi, et al., Antiproliferation, antioxidation and induction of apoptosis by *Garcinia mangostana* (mangosteen) on SKBR3 human breast cancer cell line, J. of Ethno-Pharmacology, 2004, pp. 161-166, vol. 90, abstract.

Margrain, et al., Do blue light filters confer protection against age-related macular degeneration?, Progress in Retinal and Eye Research, 2004, pp. 523-531, vol. 23, abstract.

Bailey, et al., Cerium oxide nanoparticles extend cell longevity and act as free radical scavengers, online, retrieved on Apr. 24, 2006, retrieved from http://www.med.miami.edu/mnbws/Rzigalinski11.html, abstract.

Tsai, The study of the synthesis of nano-grade cerium oxide powder, Materials Letters, 2004, pp. 2270-2274, vol. 58, abstract.

Rzigalinski, et al., Cerium oxide nanoparticles increase the lifespan of cultured brain cells and protect against free radical mechanical trauma, FASEB Journal, 2003, vol. 17, No. 4-5, page abstract No. 377.24, abstract.

Cook, et al., Neuronal damage induced by polychlorinated biphenyls is partially reversed by cerium oxide nanoparticles, online, 2003, retrieved from http://sfn.scholarone.com/itin2003/main.htm]?new_page_id=126&abstract_id=14513&p_num=669.13&is_tech=0>, retrieved on Aug. 5, 2008, abstract.

Tusnekawa, S., et al., Lattice relaxation of monosize Ce02-x nanocrystalline particles, Applied Surface Science Elsevier Netherlands, 1999, pp. 53-56, vol. 152, No. 1-2, abstract.

Hooper, et al., New treatment in age-related macular degeneration, Clinical & Experimental Opthalmology, 2003, pp. 376-391, vol. 31, abstract.

Suzuki, et al., Preparation and characteristics of magnetite-labelled antibody with the use of poly(ethylene glycol) derivatives, Biotech. and Applied Biochem., 1995, pp. 335-345, vol. 21.

(56) References Cited

OTHER PUBLICATIONS

Dong, et al., Activation of glassy carbon electrodes by dispersed metal oxide particles, Dept. of Chemistry, OSU, downloaded 2011, pp. 813, abstract.
Shui, et al., Morphological observation on cell death and phagocytosis induced by ultraviolet irradiation in a cultured human lens epithelial cell line, Exp. Eye Res., 2000, pp. 608-619, vol. 71, No. 6, abstract.
Xijuan, et al., Size-dependent optical properties of nanocrystalline Ce02:Er obtained by combustion synthesis, Phys. Chem., 2001, pp. 5266-5269, vol. 3, abstract.
Guo, Green and red upconversion luminescence in Ce02:Er3+ powders produced by 785 nm laser, Journal of Solid State Chemistry, 2007, pp. 127-131, vol. 180, No. 1, abstract.
Perez, et al., Synthesis of biocompatible dextran-coated nanoceria with pH-Dependent antioxidant properties, Small, 2008, pp. 552-556, vol. 4, No. 5, abstract.
Pirmohamed, et al., Nanoceria exhibit redox state-dependent catalase mimetic activity, Chem. Comm, 2010, pp. 2736-2738, vol. 46, abstract.
Chen, et al., Rare earth nanoparticles prevent retinal degeneration induced by intracellular peroxides, Nature Publishing Group, 2006, pp. 1-9, abstract.
Karakoti, et al., Direct synthesis of nanoceria in aqueous polyhydroxyl solutions, J. Phys. Chem. C, 2007, pp. 17232-17240, vol. 111, No. 46, abstract.
Tarnuzzer, et al., Vacancy engineered ceria nanostructures for protection from radiation-induced cellular damage, Nano Lett, 2005, pp. 2573-2577, vol. 4, No. 12, abstract.
Heckert, et al., The role of cerium redox state in the SOD mimetic activity of nanoceria, Biomaterials, 2008, pp. 2705-2709, vol. 29, abstract.
Schubert, et al., Cerium and yttrium oxide nanoparticles are neuroprotective, Biochemical and Biophysical Research Communications, 2006, pp. 86-91, vol. 342.
Zhang, et al., Cerium oxide nanoparticles: size selective formation and structure analysis, Applied Physics Letters, 2002, pp. 127-129, vol. 81, No. 1.
Patil, et al., Surface-derived nanoceria with human carbonic anhdrase II inhibitors and flourphores: a potential drug delivery device, J. Phys. Chem. C., 2007, pp. 8437-8442, vol. 111, No. 24, abstract.
Patil, et al., Synthesis of nanocrystalline ceria particles for high temperature oxidation resistant coating, Journal of Nanoparticle Research, 2002, pp. 433-438, vol. 4, abstract.
Jin, et al., Nanopartical-mediated drug delivery and gene therapy, Biotechnol. Prog, 2007, pp. 32-41, vol. 23, abstract.
Eck, et al., PEGylated gold nanoparticles conjugated to monoclonal F19 antibodies as targeted labeling agents for human pancreatic carcinoma tissue, ACS Nano, 2008, pp. 2263-2272, vol. 2, No. 11, abstract.
Nafee, Dissertation entitled "Cationically-modified nanoparticles for the polmonary delivery of the telomerase inhibitor 2'-O-Methyl RNA for the treatment of lung cancer," Dissertation zur Erlangung des Grades des Doktors der, Naturwissenschaftern der Naturwissenschaftilch-Technischen Fakul't III Chemie, Pharmazie, Bio-und Werstoffwissenschaften der Universit des Saarlandes, 2008, abstract.
Nazem, et al., Nanotechnology for Alzheimer's disease detection and treatment, Insciences J., 2011, pp. 169-193, vol. 1, No. 4, abstract.
Olivier, et al., Synthesis of pegylated immunonanoparticles, Pharmaceutical Research, 2002, pp. 1137-1143, vol. 19, No. 8, abstract.
Otsuka, et al., PEGylated nanoparticles for biological and pharmaceutical applications, Advanced Drug Delivery Reviews, 2003, pp. 403-419, vol. 55, abstract.
Qi, et al. Redispersible hybrid nanopowders; cerium oxide nanoparticle complexes with Phosphonated-PEG pligomers, ACS Nano, 2008, pp. 879-888, vol. 2, No. 5, abstract.
Sokolov, et al., Real-time vital optical imaging of precancer using anti-epidermal growth factor receptor antibodies conjugated to gold nanoparticles, Cancer Res. 2003, vol. 63, abstract.
Suh, et al., Multifunctional nanosystems at the interface of physical and life sciences, Physicaplus, 2010, issue 13, abstract.

\* cited by examiner

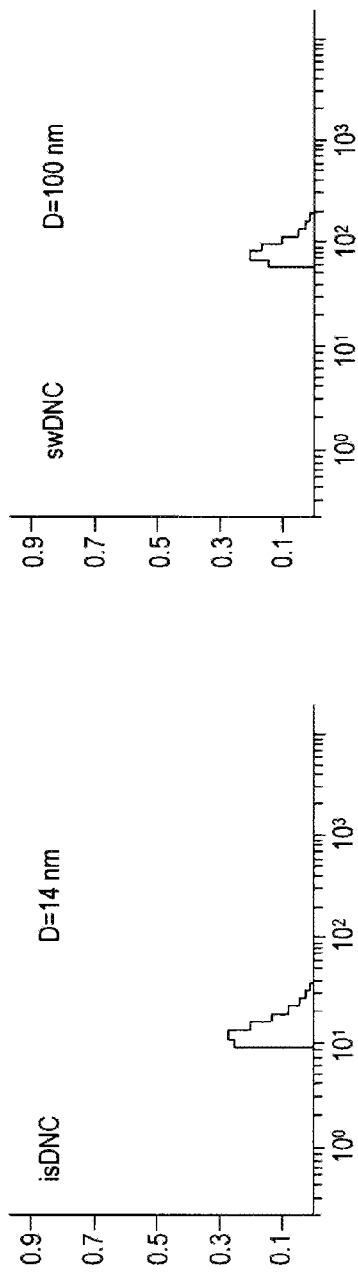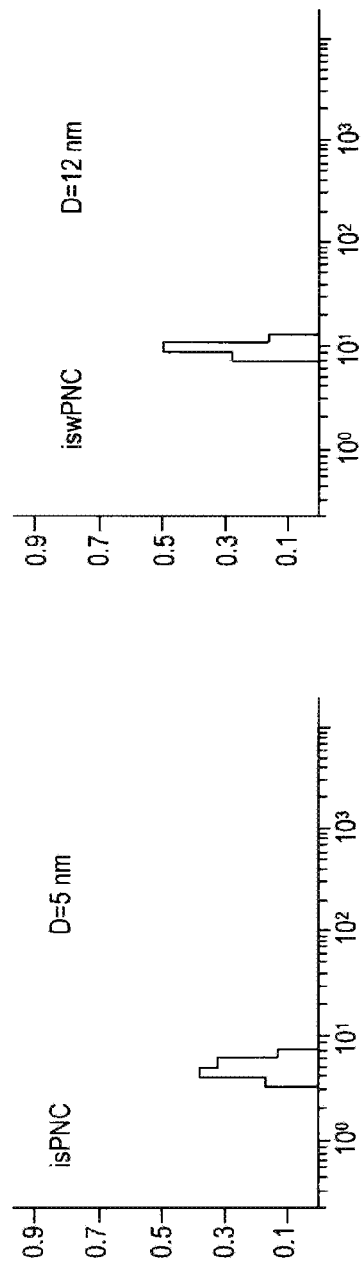
FIG. 8A  FIG. 8B  FIG. 8C  FIG. 8D

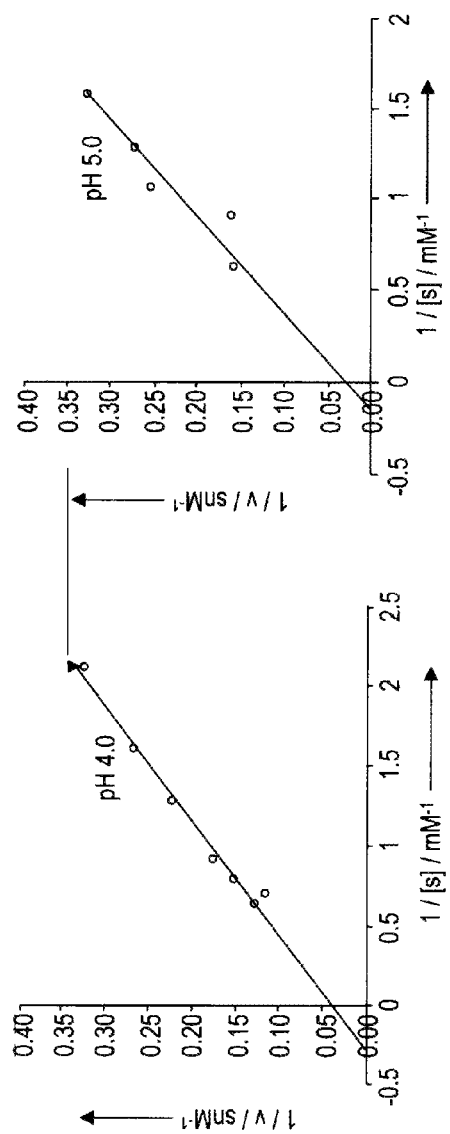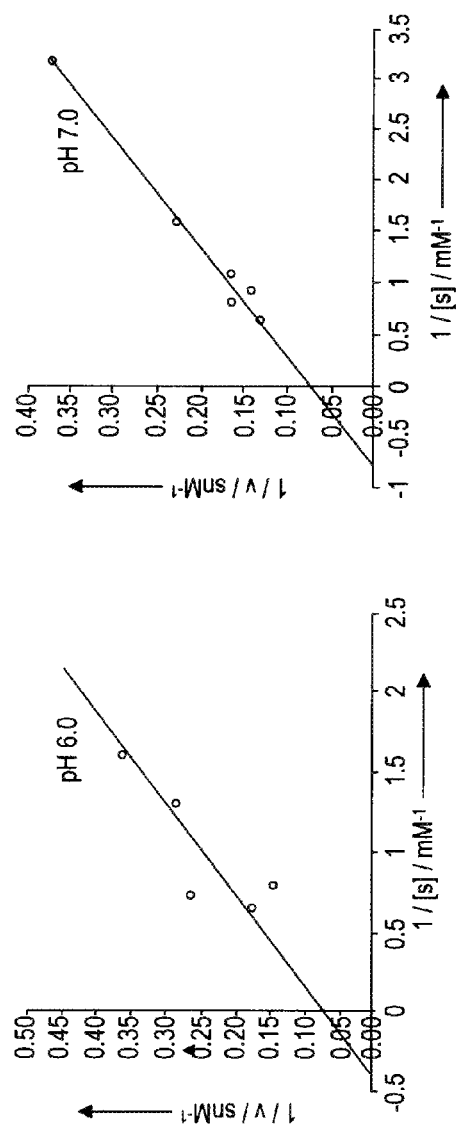
FIG. 11A  FIG. 11B  FIG. 11C  FIG. 11D

TRADITIONAL SANDWICH ELISA

NANOCERIA BASED SANDWICH ELISA

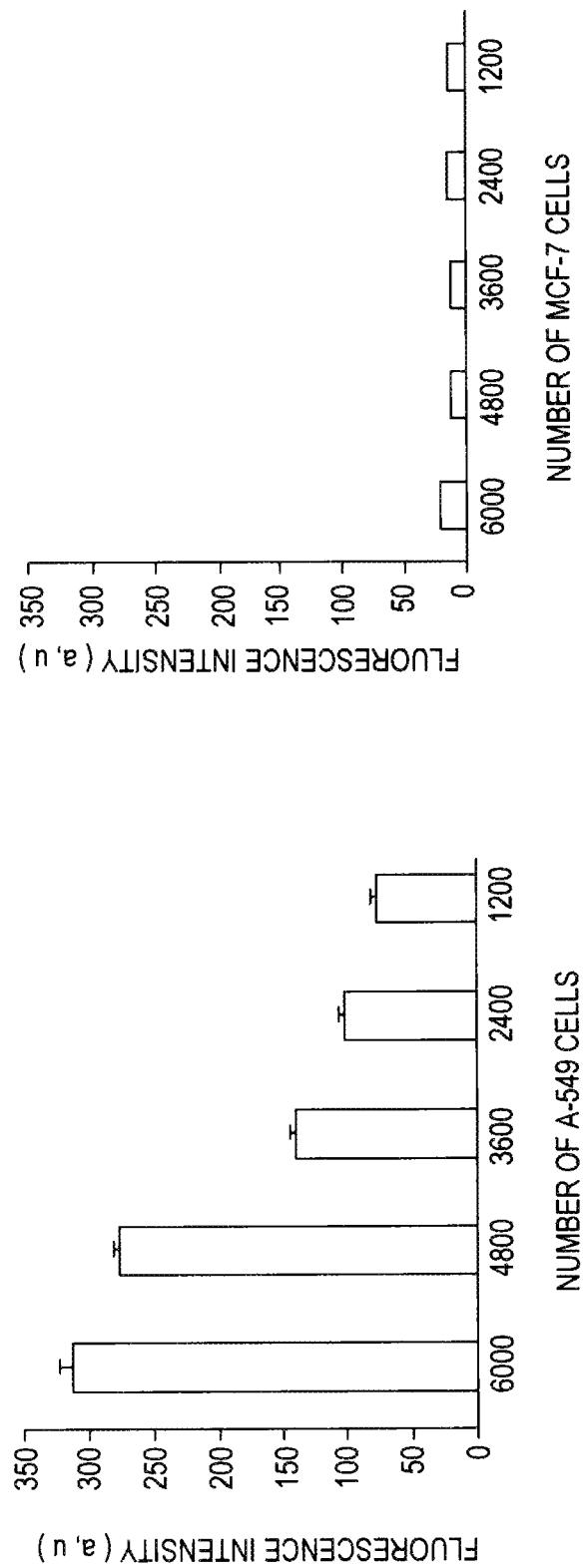

OXIDASE ACTIVITY OF POLYMERIC COATED CERIUM OXIDE NANOPARTICLES

RELATED APPLICATIONS

This invention claims the benefit of priority from U.S. Provisional Patent Application Ser. No. 61/160,744 filed on Mar. 17, 2009 which is incorporated herein by reference.

This invention was made with Government support under Agency contract number K01 CA101781 awarded by the National Institutes of Health. The government has certain rights in this invention.

FIELD OF THE INVENTION

This invention relates to uses of nanoceria particles, and in particular to methods, systems and compositions useful in the synthesis of polymer coated cerium oxide nanoparticles as an oxidizing agent and in catalytic applications.

BACKGROUND AND PRIOR ART

Unique catalytic activities have been reported in nanoscale materials in recent years, as described by D. Astruc, et al. in *Angew Chem Int Ed Engl* 2005, 44, 7852. The nanoscale or size-dependent properties are often absent in bulk materials and are the basis for designing novel catalysts with multiple applications in energy storage, chemical synthesis and biomedical applications. Cerium oxide has been used extensively in catalytic converters for automobile exhaust systems, as an ultraviolet absorber and as an electrolyte for fuel cells.

Most recently, it has been found that nanosized cerium oxide (nanoceria) possesses antioxidant activity at physiological pH and their potential use in biomedical applications such as protection against radiation damage, oxidative stress and inflammation has been reported by various researchers, such as, R. W. Tarnuzzer, et al. in *Nano Lett* 2005, 5, 2573; J. P. Chen, et al. in *Nature Nanotechnology* 2006, 1, 142; J. Niu, et al in *Cardiovasc Res* 2007, 73, 549; M. Das, et al. in *Biomaterials* 2007, 28, 1918 and J. M. Perez, et al. in *Small* 2008, 5, 552-556.

The ability of these nanoparticles to act as an antioxidant resides in their ability to reversibly switch from $Ce^{+3}$ to $Ce^{+4}$ as reported by M. Das, et al. in *Biomaterials* 2007, 28, 1918. Furthermore, the synthesis of a biocompatible dextran-coated nanoceria (DNC) preparation and enhanced stability in aqueous solution has been recently reported in co-pending U.S. patent application Ser. No. 11/965,343 filed on Dec. 27, 2007, the content of which is incorporated herein by reference; it was also reported that the polymeric coating does not affect the autocatalytic properties of nanoceria, as hydrogen peroxide and peroxyl radicals can diffuse through the hydrophilic polymer coating and oxidize $Ce^{+3}$ to $Ce^{+4}$. Thus, coated nanoceria particles are used as antioxidants in biomedical applications, such as, protection against radiation damage, oxidative stress and inflammation.

In co-pending U.S. patent application Ser. No. 12/169,179, the content of which is incorporated herein by reference; it is reported that in-situ synthesized coated nanoceria particles with enhanced biocompatibility and stability in aqueous solution exhibit a pH-dependent antioxidant activity and provide a means for tailoring reversible and non-reversible antioxidant properties of coated nanoceria particles.

A journal article by Atul Asati, Santimukul Santra, Charalambos Kaittanis, Sudip Nath, J. Manuel Perez, entitled, "Oxidase Activity of Polymer-Coated Cerium Oxide Nanoparticles" published in *Angew. Chem. Int. Ed.* 2008, 47, 2308-2312 (DOI: 10.1002/ANIE.200805279) and was subsequently published on-line Jan. 7, 2009.

It is desirable to extend the utility of the coated nanoceria particles as a stable, effective catalyst and oxidant replacing less desirable oxidants, such as, hydrogen peroxide, that are chemically unstable and harmful to biological tissue and the environment. The present invention provides a much needed solution to problems in the prior art.

SUMMARY OF THE INVENTION

A primary objective of the present invention is to provide a plurality of coated cerium oxide (ceria) nanoparticles that behave as oxidants in acidic to moderately alkaline conditions wherein the pH value is between 1 and 8.

A secondary objective of the present invention is to provide coated cerium oxide (ceria) nanoparticles with the ability to oxidize organic substrates without the need of hydrogen peroxide.

A third objective of the present invention is to provide coated cerium oxide (ceria) nanoparticles that are excellent aqueous phase redox catalyst.

A fourth objective of the present invention is to provide coated cerium oxide (ceria) nanoparticles to decompose or inactivate via oxidation processes, toxins, toxic organic compounds, such as phenols, and pesticides in wastewater treatment and toxic chemical agents, such as nerve agents.

A fifth objective of the present invention is to provide coated cerium oxide (ceria) nanoparticles that function as nanocatalyst in immunoassays, such as ELISA, where horseradish peroxidase labeled secondary antibodies are needed to facilitate the oxidation and color development of the dye.

A sixth objective of the present invention is to provide a water stable, biodegradable polyacrylic acid coated nanoceria particle wherein a small molecule can be conjugated to the polyacrylic acid coating of the nanoceria particle and used in nanoceria-based immunoassays that do not require hydrogen peroxide.

A seventh objective of the present invention is to provide coated nanoceria particles having dual functionality of binding and detection and useful as a detection tool.

An eighth objective of the present invention is to provide a coated cerium oxide (ceria) nanoparticle based immunoassay method that is easier, faster, more economical and provides greater sensitivity.

A ninth objective of the present invention is to provide coated ceria nanoparticles formed step-wise for use in improved therapeutic agents, cyto-protecting devices and detecting devices.

A preferred in situ method for the synthesis of a plurality of cerium oxide nanoparticles coated with a biodegradable polymer for antioxidant, free-radical scavenging and autocatalytic biomedical applications is also useful in the present invention, and is previously disclosed in commonly-assigned, co-pending U.S. patent application Ser. No. 12/169,179.

Further objects and advantages of the present invention will be apparent from the following detailed description of a presently preferred embodiment which is illustrated schematically in the accompanying drawings.

BRIEF DESCRIPTION OF THE FIGURES

FIG. 8A shows the average hydrodynamic diameter distribution of approximately 14 nm for in-situ synthesized dextran coated nanoceria of the present invention using dynamic light scattering (DLS).

FIG. 8B shows the average hydrodynamic diameter distribution of approximately 100 nm for step-wise synthesized dextran coated nanoceria of the present invention using dynamic light scattering (DLS).

FIG. 8C shows the average hydrodynamic diameter distribution of approximately 5 nm for in-situ synthesized polyacrylic acid (PAA) coated nanoceria of the present invention using dynamic light scattering (DLS).

FIG. 8D shows the average hydrodynamic diameter distribution of approximately 12 nm for step-wise synthesized polyacrylic acid (PAA) coated nanoceria of the present invention using dynamic light scattering (DLS).

FIG. 10B is a graph of polymer coated nanoceria's ability to oxidize 2,2-azinobis-(3-ethylbenzothizoline-6-sulfonic acid) (AzBTS) with the following nanoparticle sizes in-situ PNC (5 nm), step-wise PNC (12 nm), in-situ DNC (14 nm) and step-wise DNC (100 nm), showing that the small size ceria nanoparticles show higher oxidase activity than large size nanoparticles.

FIG. 11A is a double reciprocal plot of oxidase activity of polymer coated nanoceria at pH 4.0 using 3,3',5,5'-tetramethyl benzidine (TMB) as substrate providing a steady state kinetic assay.

FIG. 11B is a double reciprocal plot of oxidase activity of polymer coated nanoceria at pH 5.0 using 3,3',5,5'-tetramethyl benzidine (TMB) as substrate providing a steady state kinetic assay.

FIG. 11C is a double reciprocal plot of oxidase activity of polymer coated nanoceria at pH 6.0 using 3,3',5,5'-tetramethyl benzidine (TMB) as substrate providing a steady state kinetic assay.

FIG. 11D is a double reciprocal plot of oxidase activity of polymer coated nanoceria at pH 7.0 using 3,3',5,5'-tetramethyl benzidine (TMB) as substrate providing a steady state kinetic assay.

FIG. 25A is a graph of the fluorescence intensity when monitoring the expression of folate receptor on folate positive lung carcinoma cell line.

FIG. 25B is a graph of the fluorescence intensity when monitoring the expression of MCF-7 breast carcinoma cell lines which do not express the folate receptor; this graph is used as a control.

DESCRIPTION OF THE PREFERRED EMBODIMENTS

Figure 1A:
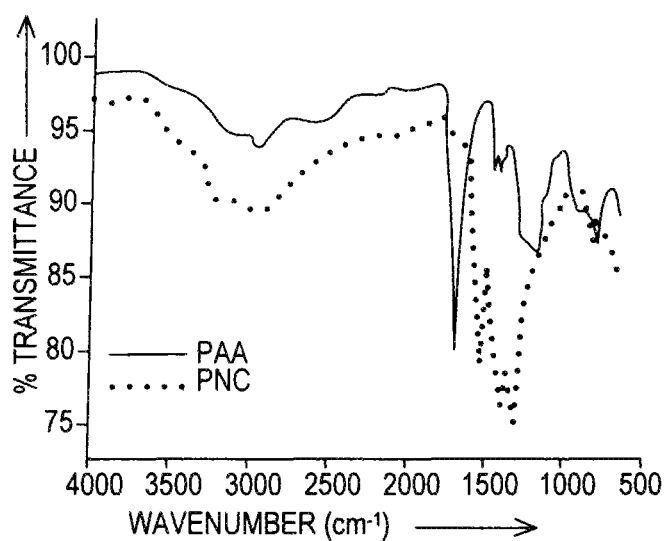
FIG. 1A is a Fourier Transform Infrared (FT-IR) spectra showing the presence of characteristic infrared (IR) bands of both polyacrylic acid (PAA) and PAA coated nanoceria (PNC) confirming that the polymer coating is an integral part of nanoceria.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Ampliflu is the common chemical name for (10-acetyl-3,7-dihydroxy-phenoxazine), a chromogenic fluorescent dye.

AzBTS is the chemical abbreviation for 2,2-azinobis-(3-ethylbenzothizoline-6-sulfonic acid)

The term "chromogenic" is used to refer to compound that contains a chromophore and is capable of becoming a dye it is used herein in combination with the term "colorimetric"

The term "colorimetric" is used to refer to a dye compound that is useful in chemical analysis wherein there is a comparison of a liquid's color with standard colors.

DNC is the acronym used herein to mean dextran coated nanoceria. Dextran is a complex, branched polysaccharide made of many glucose molecules.

The term "fluorescent" is used to refer to a dye compound that is useful in a fluorimetric analytical process wherein measurements of fluorescence and related phenomena, such as intensity or radiation are observed; the observation of fluorescence is commonly described as bright and glowing.

OPD is the chemical abbreviation for ortho-phenylene diamine, a chromogenic fluorescent dye.

PAA is the acronym used herein to mean polyacrylic acid.

PNC is the acronym used herein to mean polyacrylic acid coated nanoceria.

TMB is the chemical abbreviation for 3,3',5,5'-tetramethyl benzidine.

The term "biocompatible polymer" is used herein to describe a class of polymers that are non-toxic to mammals and the environment and more specifically, include dextran, derivatives of dextran such as reduced dextran, carboxylmethyl reduced dextran, a polyol polymer or carbohydtrate polymer, synthetic polyols, carboxylated polymers, such as polyacrylic acid, and other polysaccharides, such as, but not limited to, arabinogalactan, and chitosan as disclosed in Groman et al. U.S. Patent Publication 2006/0014938 and Gaw et al. U.S. Patent Publication 2003/0124,194.

The term "click chemistry" used herein, is a chemical philosophy introduced by K. Barry Sharpless of Scripps Research Institute in 2001 and describes chemistry tailored to generate substances quickly and reliably by joining small units together under simple reaction conditions resulting in high chemical yield.

The term "coated nanoceria" is used herein to refer to cerium oxide nanoparticles coated with any bio-compatible polymer useful in the present invention. For purposes of illustration, but not as a limitation, the two polymeric coatings discussed in the examples are polyacrylic acid and dextran (a polysaccharide).

"ELISA" is the acronym for Enzyme-Linked ImmunoSorbent Assay which is a biochemical technique used to evaluate either the presence of antigen or the presence of antibody, such as with the HIV test or West Nile Virus. ELISA is a diagnostic tool in medicine and plant pathology, as well as a quality control check in various industries. For example, in the food industry, ELISA is used to detect food allergens such as milk, peanuts, walnuts, almonds, and eggs.

The term "nanoceria" is used interchangeably with "cerium oxide nanoparticles" and is used to refer to the cerium oxide particles of multiple valences.

The term "nanocrystal" is used interchangeably with "nanoparticle."

In the present invention, the cerium oxide nanoparticles or nanoceria are polymer associated, or, in other words, coated with a bio-compatible polymer. The polymer confers stability in water and can be functionalized with carboxylic or amino groups for conjugation with proteins, peptides, oligonucleotides, small molecules, and the like.

Further, as will be explained in detail, the oxidant activity of the coated nanoceria particles is facilitated in an acidic pH, from approximately 1 to approximately 4 when a colorimetric/chromogenic dye is used as the substrate; whereas, in an acidic to moderately alkaline pH, from approximately 4.0 to approximately 8.0, oxidant activity of the coated nanoceria particles is facilitated when a colorimetric/chromogenic/fluorescent dye is used as the substrate. In a pH range from approximately 8 to approximately 11, the coated nanoceria particle does not function as an oxidant, unless there are changes made to the dye substrate, thus permitting the design of improved catalysts, oxidizing agents and detection devices.

In general, the plurality of coated nanoceria particles of the present invention each have a size between approximately 1 nanometer (nm) to approximately 500 nm in diameter, preferably between approximately 7 nm and approximately 100 nm. For example, the coated nanoceria particles used herein are composed of a cerium oxide core that is approximately 4 nanometers (nm) in diameter surrounded by a dextran coating for a total nanoparticle size of approximately 10 nm in diameter, as disclosed in U.S. patent application Ser. No. 12/169,179, which is incorporated herein by reference.

Briefly, the in-situ synthesis of coated nanoceria in U.S. patent application Ser. No. 12/169,179 consists of mixing an aqueous solution of cerium nitrate and dextran and adding the mixture to an ammonia solution under continuous stirring. Upon formation of the cerium oxide nanocrystals, molecules of dextran coat the nanoparticle surface, preventing further growth and resulting in dextran coated nanoceria.

The present invention provides a step-wise method and procedure for synthesizing a biodegradable polymer coated ceria nanoparticle having a thicker coating of the ceria nanoparticle than the coating obtained using the in-situ synthesis method. The thicker coating allows the oxidase activity to be tuned or adjusted because a thicker coating results in a slower oxidase activity and a thinner coating allows for faster oxidase activity of the coated ceria nanoparticle.

Also, the nature and molecular weight of the polymer plays a role in the thickness of the coating. In the examples provided herein, the molecular weight of polyacrylic acid is approximately 1,000 and the molecular weight of dextran is approximately 10,000. Therefore, one would obtain on average a thicker coating of dextran as opposed to polyacrylic acid. Controlling the thickness of the polymer coating on nanoceria would result in a better control of the catalytic activity or oxidase at acidic pH and antioxidant activity at neutral pH of the coated nanoceria. Similar tunability of the oxidase activity occurs with in-situ synthesized biodegradable polymer coated ceria nanoparticles when a large molecular weight polymer is used to coat the ceria nanoparticle; the larger the molecular weight, the slower the rate of oxidase activity.

The examples below provide further detail on the synthesis and physical characterization of the biodegradable polymer coated ceria nanoparticles of the present invention. Polyacrylic acid (PAA) and dextran, a polysaccharide, are used as exemplary polymeric coatings and are not a limitation of the present invention; other bio-compatible polymers may be judicially selected by a person of skill in the art. Also, in the examples below, the sensitive colorimetric/chromogenic organic dyes chosen are 3,3',5,5'-tetramethyl benzidine (TMB) and 2,2-azinobis-(3-ethylbenzothizoline-6-sulfonic acid) (AzBTS); however, it is understood that these chromogenic dyes for horseradish peroxidase (HRP) are only representative of dyes used in detection and analysis methods. Other chromogenic substrates for HRP can be used; other sensitive dyes can be used and include, but are not limited to chromogenic, fluorescent, photoluminescent substrates of a peroxidase or an oxidase. It has been determined that sensitive dyes that combine the chromogenic and fluorescent properties extend oxidant activity of nanoceria particles in the pH range from acidic to moderately alkaline, i.e., pH 4 to pH 8. The extended pH range of oxidase activity is important for use on substrates that are unstable in low pH conditions, such as pH values of 1 to 4.

Herein, coated nanoceria is reported to have an intrinsic oxidase activity at acidic pH. Since nanoceria possess a higher ratio of $Ce^{+4}$ to $Ce^{+3}$ at pH 4, it is found to behave as an oxidant in slightly acidic conditions. In fact, nanoceria behaves as an oxidant at pH 4 as it can quickly oxidize a series of organic substrates without an oxidizing agent, such as, hydrogen peroxide. The observed activity is not only pH-dependent, but also dependent on the size of the cerium oxide nanoparticles, as well as the thickness of the polymer coating.

Based on the above findings, an immunoassay is designed in which a folate-conjugated cerium oxide nanoparticle provides dual functionality of binding to folate expressing cancer cells and detection via catalytic oxidation of sensitive colorimetric substrates/dyes. The unique pH-dependent oxidase activity of coated cerium oxide nanoparticles in aqueous media makes them a powerful tool for wide range of potential applications in biotechnology and environmental chemistry.

EXAMPLE 1

In-Situ Synthesis of Dextran Coated Ceria Nanoparticles (DNC) and Polyacrylic Acid-Coated Ceria Nanoparticles (PNC)

Under ambient conditions, a 1 M cerium nitrate (Aldrich, 99%) solution (2.17 g in 5 ml of water) was mixed with a 1.0M Dextran T-10 (Sigma) (5 g in 10 ml of water) to form mixture (I) comprising a plurality of ceria nanoparticles.

Alternately, if preparing polyacrylic acid (PAA) coated nanoceria, 0.5 M solution of polyacrylic acid (PAA) (Sigma) is used instead of 1.0M Dextran T-10 to form mixture (I).

Under continuous stirring, the mixture (I) is then added dropwise to 30 ml of 29% ammonium hydroxide solution (Fischer, USA) forming mixture (II). Mixture (II) is then stirred continuously for 24 hours. After 24 hours of stirring, the solution turns from a light yellow to a deep brown color indicating the formation of stabilized dextran or PAA coated-nanoceria. The preparation is centrifuged at a rate of 4000 rpm for two 30-minute cycles to settle down any debris and large agglomerates. The supernatant solution is then purified by removal of free polyacrylic acid (PAA) or dextran by ultrafiltration using a 30 K Amicon cell (Millipore Inc.).

EXAMPLE 2

Step-Wise Synthesis of Dextran Coated Ceria Nanoparticles (DNC) and Polyacrylic Acid-Coated Ceria Nanoparticles (PNC)

For stepwise synthesis, a solution containing 1M cerium (III) nitrate (2.17 g in 5.0 ml of water) was added under continuous stirring to 30.0 ml ammonium hydroxide solution. Then, after one minute, 0.5 M solution of PAA, if preparing a polyacrylic aicd (PAA)-coated ceria nanoparticle (PNC) or 1.0 M dextran solution, if preparing a dextran coated ceria nanoparticle (DNC) is added and allowed to stir for 3 hours. Purification and subsequent processing steps are the same as in-situ method. A thicker polymer coating results with the step-wise preparation that omits the separate steps of forming a mixture (I) and adding mixture (I) dropwise to mixture (II).

Figure 1B:
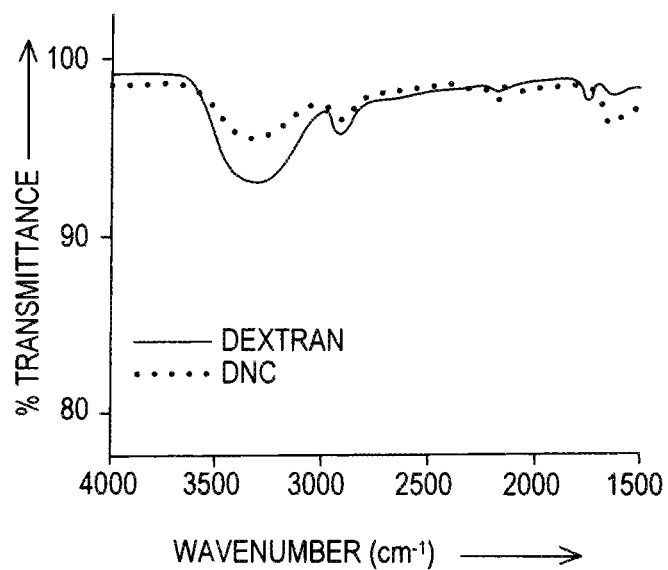
FIG. 1B is a Fourier Transform Infrared (FT-IR) spectra showing the presence of characteristic infrared (IR) bands of both dextran polymer and dextran coated nanoceria (DNC) confirming that the dextran coating is an integral part of nanoceria.

For both preparations, the PAA or DNC polymer coating is confirmed by performing the Fourier Transform Infrared (FT-IR) analysis on the dry sample of preparations as shown in FIG. 1A showing the presence of characteristic IR bands of both polyacrylic acid (PAA) and PAA coated nanoceria (PNC) confirming that the polymer coating is an integral part of nanoceria particles, since characteristic IR peaks of PAA are also present in the PAA-coated nanoceria spectrum and FIG. 1B showing the presence of characteristic IR bands of both dextran alone and dextran coated nanoceria (DNC) confirming that the polymer coating is an integral part of nanoceria, since characteristic IR peaks of dextran are also present in the dextran-coated nanoceria (DNC) spectrum.

EXAMPLE 3

Oxidation of Organic Dyes at Low pH

In a first set of experiments, a DNC preparation discussed by J. M. Perez et al. in *Small* 2008, 4, No. 5, 552-556 is used to facilitate the oxidation of a series of organic dyes at low pH. In these experiments, 3,3',5,5'-tetramethyl benzidine (TMB) and 2,2-azinobis-(3-ethylbenzothizoline-6-sulfonic acid) (AzBTS), are selected and oxidation develop either a blue (TMB) or green (AzBTS) color in aqueous solution. These dyes are typically used as horseradish peroxidase (HRP) substrates in various bioassays and most recently they have been used to demonstrate the peroxidase activity of iron oxide nanoparticles, as reported by L. Z. Gao, et al. in *Nature Nanotechnology* 2007, 2, 577. However, in these peroxidase-catalyzed reactions, hydrogen peroxide ($H_2O_2$) is required as the electron acceptor or oxidizing agent.

Figure 2:
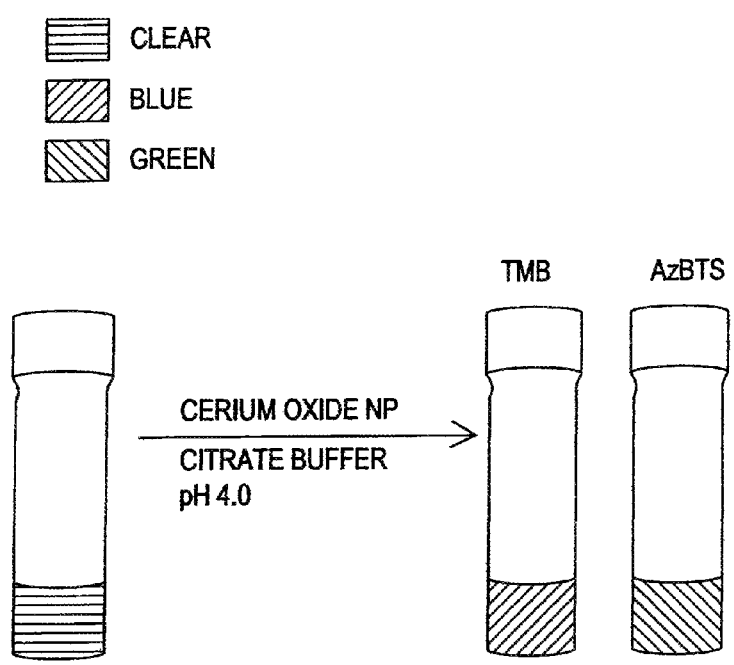
FIG. 2 shows separate vials of dextran coated nanoceria (DNC)-catalyzed oxidation of 3,3',5,5'-tetramethyl benzidine (TMB), in the absence of hydrogen peroxide, at pH 4.0 yielding a blue color and dextran coated nanoceria (DNC)-catalyzed oxidation of 2,2-azinobis-(3-ethylbenzothizoline-6-sulfonic acid) (AzBTS), in the absence of hydrogen peroxide, at pH 4.0 yielding a green color.

In contrast, it is found that DNC catalyzes the fast oxidation (within minutes) of both TMB and AzBTS in the absence of hydrogen peroxide, as judged by the appearance of the characteristic color upon addition of the dyes to citrate-buffered solutions of coated ceria nanoparticles at pH 4.0, as shown in FIG. 2. In FIG. 2, a citrate-buffered solution of coated cerium oxide nanoparticles begins as a solution with a clear color and when TMB is added, the solution changes to a blue color indicating the oxidation of 3,3',5,5'-tetramethyl benzidine (TMB). Likewise, when AzBTS is added to the clear solution of citrate-buffered coated cerium oxide nanoparticles, the solution changes to a green color indicating the oxidation of 2,2-azinobis-(3-ethylbenzothizoline-6-sulfonic acid).

Figure 3A:
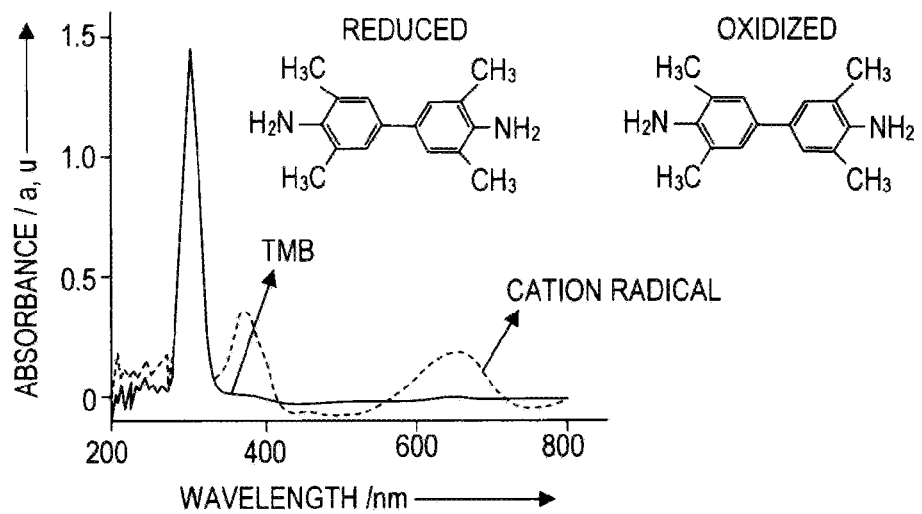
FIG. 3A is a graph of the UV visible spectrum exhibited during polymer coated nanoceria mediated oxidation of 3,3',5,5'-tetramethyl benzidine (TMB) to a blue cation radical with characteristic peaks at 370 nm wavelength and 652 nm wavelength. The peak at 370 nm corresponds to the yellow color state which remains for only a few seconds.

Further evidence of the oxidase activity of the dextran-coated nanoparticles (DNC) is shown by the corresponding UV-visible spectrum. In FIG. 3A, TMB (3,3',5,5'-tetramethyl benzidine) (TMB) is oxidized to form a blue cation radical with characteristic peaks at 370 nm and 652 nm wavelength. The peak at 370 nm corresponds to the yellow color state which remains for only a few seconds and the peak at 652 nm indicates the stable blue color, the change to the blue color occurs within two minutes. Moreover, TMB can be completely oxidized using a higher concentration of nanoceria to the corresponding di-imine product which gives a characteristic peak at 450 nm with complete yellow color (not shown).

Figure 3B:
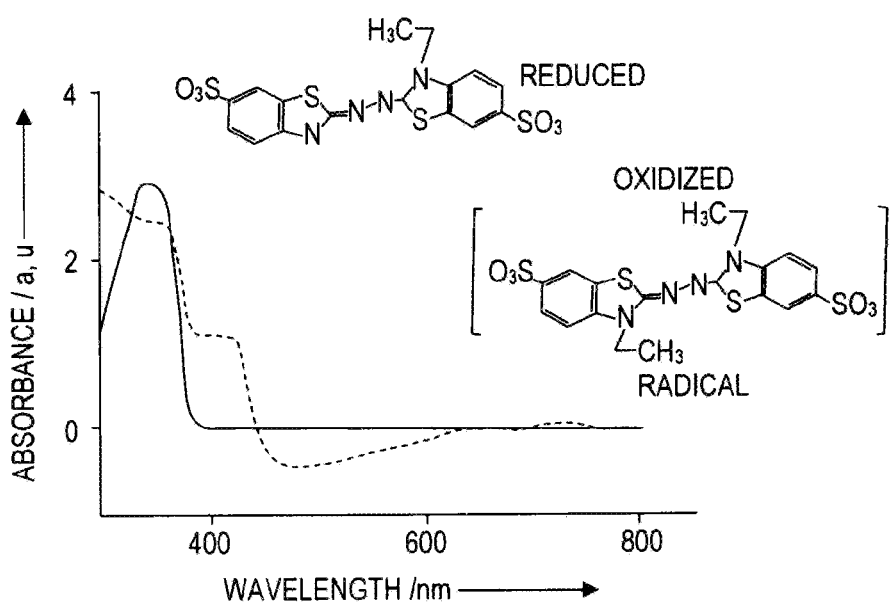
FIG. 3B is a graph of the UV visible spectrum exhibited during polymer coated nanoceria mediated oxidation of 2,2-azinobis-(3-ethylbenzothizoline-6-sulfonic acid) (AzBTS), to a green cation radical with characteristic peak at 475 mu wavelength.

The UV-visible spectrum in FIG. 3B for 2,2-azinobis-(3-ethylbenzothizoline-6-sulfonic acid) (AzBTS) oxidation gives a green color radical cation at 475 nm. The entire transformation takes place within 2 minutes which explains the fast kinetic of coated nanoceria mediated oxidation.

Figure 4:
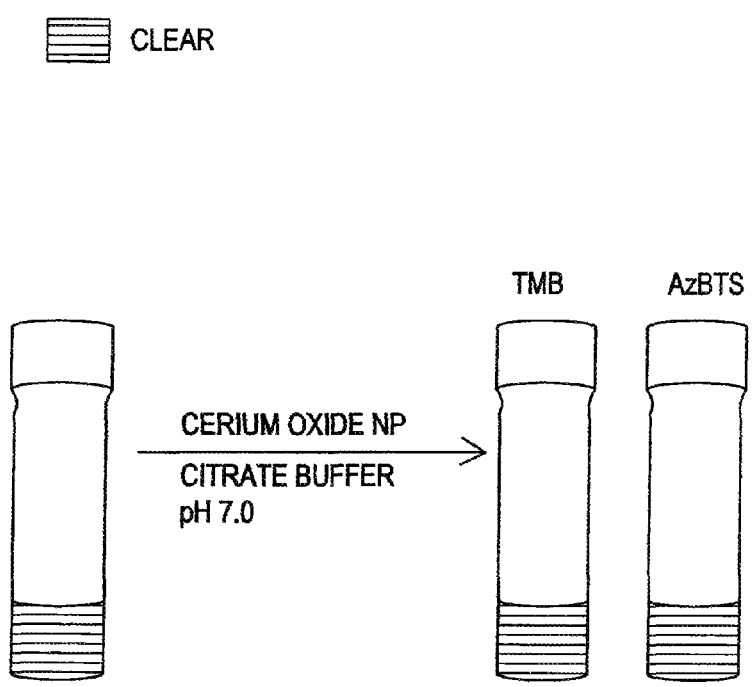
FIG. 4 shows the absence of color development indicating no significant oxidation of TMB or AxBTS at pH 7.0 after the addition of polymer coated nanoceria, even in the presence of hydrogen peroxide and overnight incubation.

Meanwhile, at pH 7.0, no significant oxidation of TMB or AzBTS is observed, even in the presence of hydrogen peroxide or upon overnight incubation, as judged by the absence of color development when TMB and AzBTS are added to cerium oxide nanoparticles in a citrate buffered solution at a neutral pH 7.0 as shown in FIG. 4. The solution remains clear or colorless at neutral pH, indicating that no oxidation has occurred.

EXAMPLE 4

Oxidation Properties Decrease with Increase in pH

Figure 5:
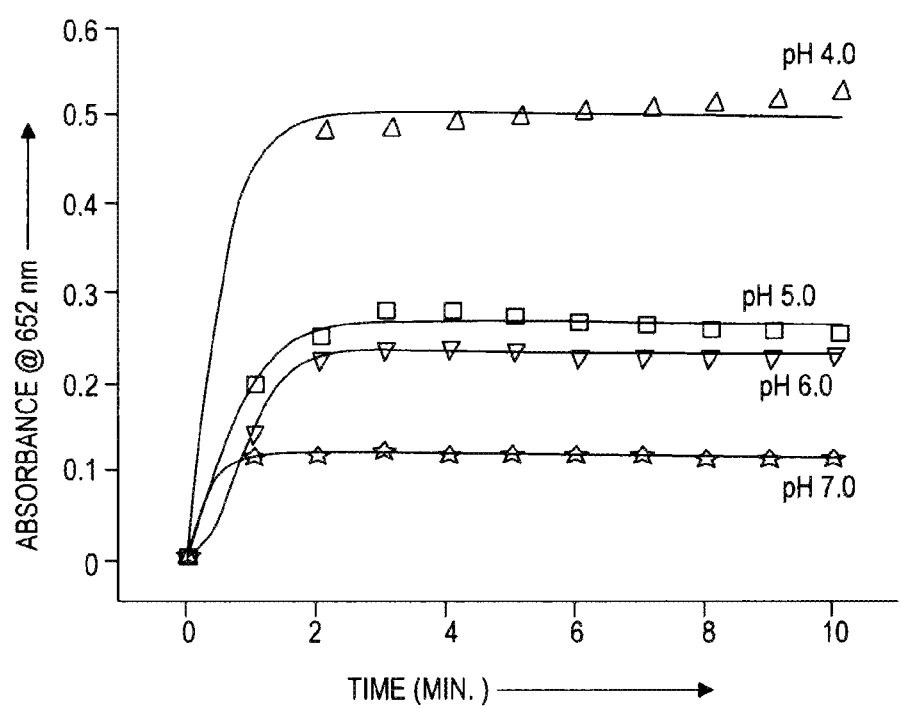
FIG. 5 shows DNC-catalyzed oxidation of 3,3',5,5'-tetramethyl benzidine (TMB), in the absence of hydrogen peroxide, at pH 4.0, pH, 5.0, pH 6.0 and pH 7.0.

Furthermore, pH-dependent studies of the DNC-catalyzed oxidation of TMB show that as the pH of the buffered solution increases from pH 4.0 to 7.0, the ability of DNC to oxidize the dye decreases as shown in FIG. 5. At pH 4.0 the absorbance at 652 nm for DNC catalyzed oxidation of TMB is approximately 0.5 after two minutes and remains stable for more than 10 minutes. At pH 5.0, absorbance at 652 nm is approximately 0.25 after two minutes and remains stable for more than 10 minutes. At pH 6.0, absorbance is approximately 0.2 after two minutes and remains stable for more than 10 minutes. At pH 7.0, absorbance is approximately 0.1 after 2 minutes and remains stable for more than 10 minutes—at this absorbance level, there is no color change. These results suggest that DNC behaves as an oxidizing agent in a pH-dependent manner, being most optimal at acidic pH.

EXAMPLE 5

Oxidation of Dopamine (DOPA)

Figure 6:
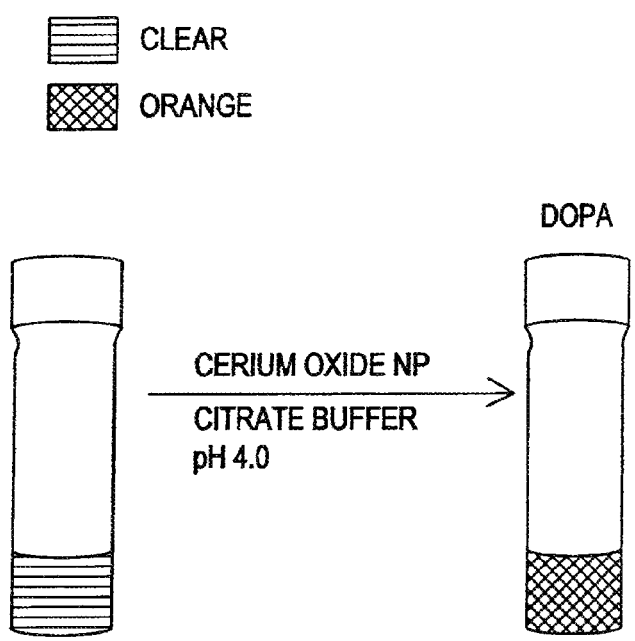
FIG. 6 is a drawing of vials of polymer coated nanoceria catalyzed oxidation of Dopamine (DOPA) to an orange color aminochrome in citrate buffer at pH 4.0.
Figure 7:
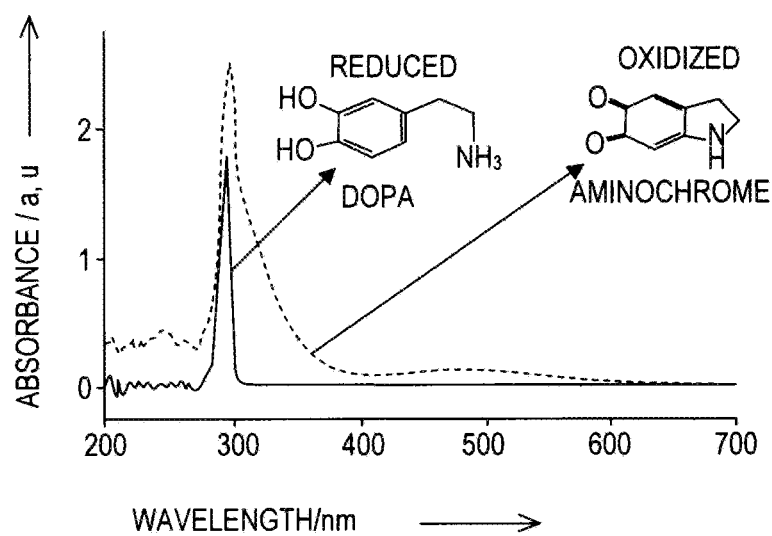
FIG. 7 is a graph of UV visible spectrum exhibited during polymer coated nanoceria mediated oxidation of DOPA to orange aminochrome with a characteristic band at 475 nm wavelength.

To further verify the ability of coated nanoceria to behave as an oxidation nanocatalyst, dopamine (DOPA), a catecholamine difficult to oxidize at low pH was chosen. Results show that DNC facilitated the oxidation of DOPA in a citrate buffered solution at pH 4.0 within minutes, producing the characteristic orange color corresponding to aminochrome, one of the major oxidation products of DOPA as shown in FIG. 6. Dextran coated nanoceria (DNC) in a citrate buffered solution at pH 4.0 is a clear, colorless solution and with the addition of dopamine (DOPA), within minutes an orange color appears. The formation of aminochrome by DNC was confirmed by UV-visible light spectrum studies which show the appearance of the characteristic band at 475 nm indicating the formation of aminochrome as shown in FIG. 7. In the absence of DNC, no apparent oxidation of DOPA occurs at pH 4.0, even after days of incubation. This is in contrast to DOPA solutions in water or citrate buffer pH 7.0, where DOPA slowly auto-oxidizes, developing the characteristic reddish-brown color after overnight incubation (16 hours). Taken together, the results demonstrate that DNC can be employed for the oxidation of sensitive dyes and is also able to catalyze the oxidation of various organic molecules at acidic pH, even difficult to oxidize organic compounds, such as dopamine (DOPA).

It has been well established that the catalytic properties of nanomaterials often depend upon the size of the nanocrystal, as discussed by M. Shokouhimehr, et al. in *Angew. Chem. Int. Ed Engl.* 2007, 46, 7039. However, studies on the effect of polymer coating thickness surrounding the nanoparticles are less common. In the present invention, a study of coated nanoceria-catalyzed oxidation of dyes is undertaken to determine if oxidation is also size- and polymer-coating-thickness-dependent. Previously reported dextran-coated nanoceria (DNC) preparation was synthesized via an in-situ procedure reported by J. M. Perez et al in *Small* 2008 supra in which the dextran (10 kDa) is present in solution at the time of the initial formation of the cerium oxide nanocrystals. Under these conditions, the polymer influences both the nucleation and growth of the initial nanocrystal, resulting in nanoparticles with a small nanocrystal core surrounded by a thin polymeric coating. In the case of DNC, we have obtained nanoparticles with a cerium oxide core of 4 nm surrounded by a thin coating of dextran for a total nanoparticle size (hydrodynamic diameter) of 14 nm.

In the present invention, a step-wise procedure for synthesizing coated ceria nanoparticles is used. In a first step, the ceria nanoparticles are formed; then, in a second step, the polymer is added at a specific time after initial formation of the nanoparticles. A step-wise method has been previously reported for the synthesis of coated iron oxide nanoparticles, yielding iron-oxide nanoparticles with a thicker polymer coating as compared to an in-situ process according to H. Lee et al in *Journal of the American Chemical Society* 2006, 128, 7383. In addition, slightly larger nanocrystal cores are also obtained using this method.

Therefore, to study the effect of the polymeric coating thickness on the catalytic activity of nanoceria, dextran coated nanoparticles (DNC) were synthesized using a step-wise method. In this method the dextran polymer was added 60 seconds after initial formation of the nanocrystals, to yield a step-wise DNC (swDNC) nanoparticle preparation with average hydrodynamic diameter of 100 nm, as shown in FIG. 8B which is approximately 10 times larger than the DNC nanoparticles obtained with the in-situ method (isDNC), shown in FIG. 8A with an average hydrodynamic diameter of 14 nm.

In addition, a coated nanoceria was synthesized using polyacrylic acid (1.8 kDa). The use of a smaller molecular weight polymer in the synthesis of coated nanoceria is advantageous because it would allow the formation of nanoparticles with an even thinner coating than those obtained with dextran (10 kDa) using either the in-situ or step-wise method. Dynamic light scattering experiments show that for the in situ polyacrylic-acid-coated nanoceria preparations (isPNC), the average hydrodynamic diameter of the nanoparticles was 5 nm, as shown in FIG. 8C. Meanwhile, for the stepwise preparation (swPNC), a value of 12 nm was obtained as shown in FIG. 8D.

As hypothesized, smaller nanoparticles with a thinner polymer coating were obtained using the 1.8 kDa polyacrylic acid polymer. It is also possible to prepare thicker polymer coatings on ceria nanoparticles synthesized in-situ using a suitable polymer with a higher molecular weight.

EXAMPLE 6

Effect of Coating Thickness on Oxidation of TMB

Figure 9:
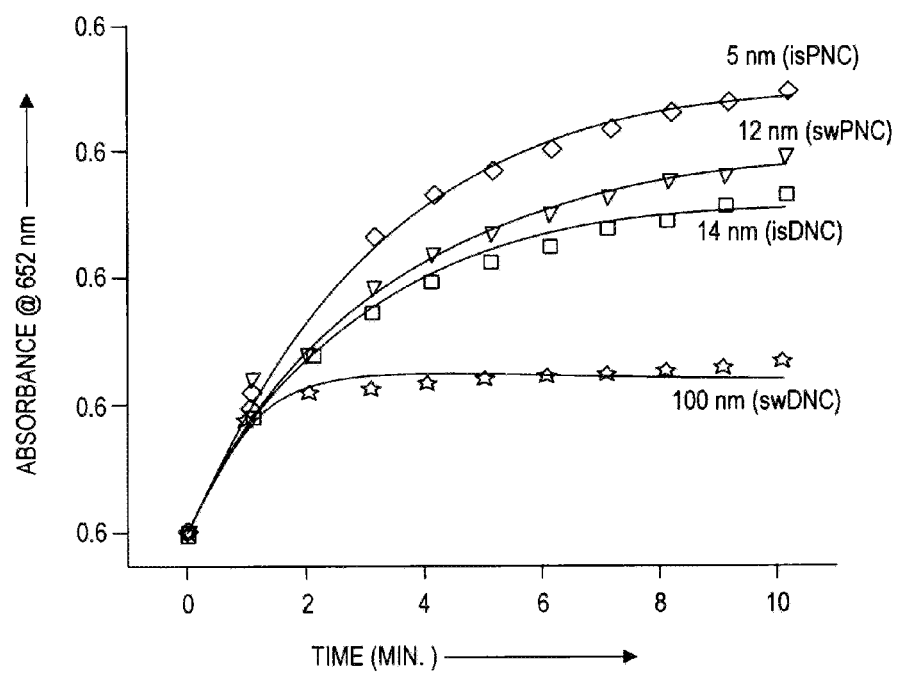
FIG. 9 is a graph of coated nanoceria's ability to oxidize 3,3',5,5'-tetramethyl benzidine (TMB), with the following nanoparticle sizes in-situ PNC (5 nm), step-wise PNC (12 nm), in-situ DNC (14 nm) and step-wise DNC (100 nm), showing that the small size ceria nanoparticles show higher oxidase activity than large size nanoparticles.

Various preparations of coated nanoceria were used to perform kinetic studies and assess the effect of the coating thickness and nanoparticle size on the catalytic activity of nanoceria. Results show that nanoceria's ability to oxidize 3,3',5,5'-tetramethyl benzidine (TMB) varies with nanoparticle size in the order isPNC (5 nm)>swPNC (12 nm)>isDNC (14 nm)>swDNC (100 nm). Interestingly, the nanoparticles composed of a thin polyacrylic acid coating have a higher catalytic activity than those composed of a thicker dextran coating as shown in FIG. 9. This might be attributed to the fact that coated nanoceria with a thin and permeable polyacrylic acid-coating can facilitate the transfer of molecules in and out of the nanoceria core surface faster than a thicker coating.

Figure 10A:
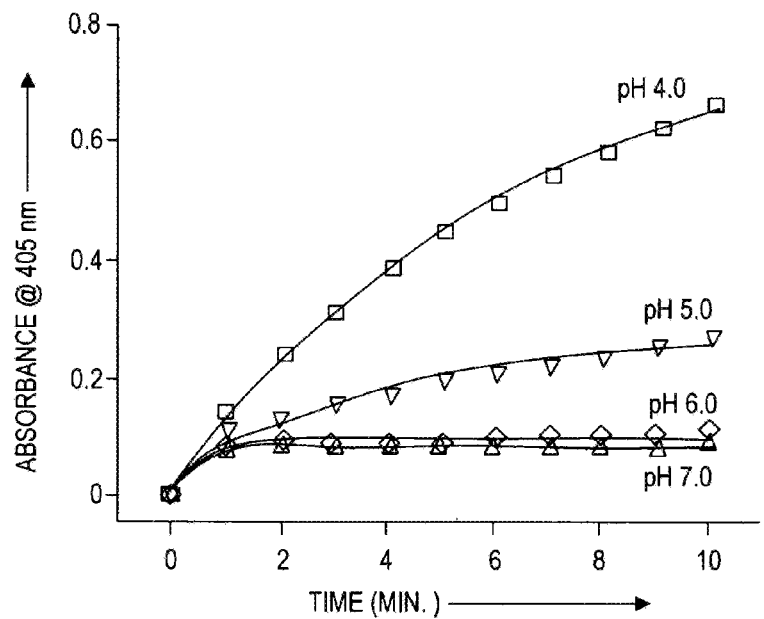
FIG. 10A is a graph of polymer coated nanoceria's ability to oxidize 2,2-azinobis-(3-ethylbenzothizoline-6-sulfonic acid) (AzBTS) at pH4.0, pH 5.0, pH 6.0 and pH 7.0 at room temperature for a period of approximately ten minutes.
Figure 10A:
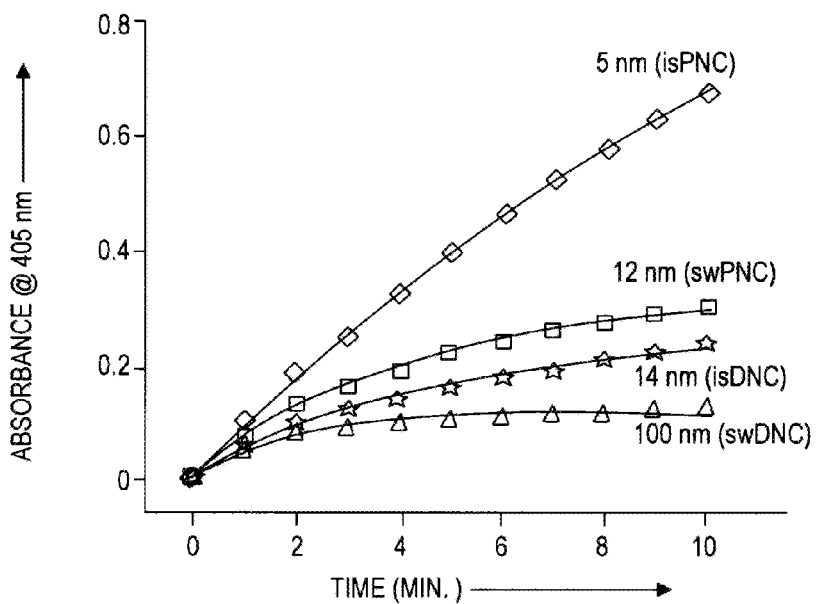

Similar experiments were performed with 2,2-azinobis-(3-ethylbenzothizoline-6-sulfonic acid) (AzBTS) which shows similar behavior to TMB. First, with regard to pH values, in FIG. 10A, oxidation of AzBTS is pH-dependent with optimum activity at pH 4.0, carried out at room temperature. Under the same conditions, small size coated ceria nanoparticles show higher oxidase activity than large size coated ceria nanoparticles as shown in FIG. 10B. When measuring absorbance at 405 nm, the 5 nm size in-situ synthesized polyacrylic acid-coated nanoparticles (isPNC) show the highest oxidase activity in nanoceria-promoted oxidation of AzBTS in comparison to the 100 nm size step-wise dextran coated nanoceria (swDNC).

EXAMPLE 7

Effect of Nanoparticle Size on Oxidation of TMB

The steady state kinetic parameters for the nanoceria-catalyzed oxidation of TMB were determined. Typical Michaelis-Menten curves were obtained for both PNC and DNC. Double reciprocal plots of oxidase activity are shown at pH 4.0 in FIG. 11A, at pH 5.0 in FIG. 11B, at pH 6.0 in FIG. 11C and at pH 7.0 in FIG. 11D.

Furthermore, kinetic studies of nanoceria (isPNC) at various pH values indicate faster kinetics at acidic pH ($K_m$ 3.8, $V_{max}$ 0.7) and much slower kinetics at neutral pH ($K_m$ 1.3, $V_{max}$ 0.1) as shown in Table 1 below. These results contrast to those obtained using the enzyme HRP or iron oxide nanoparticles where slower kinetics are reported even in the presence of hydrogen peroxide; see L. Z. Gao et al. *Nature Nanotechnology* 2007 supra

TABLE 1

Nanoceria's oxidase kinetics are pH-dependent[a]

| pH | $K_m$ (mM) | $V_{max}$ (µM/s) |
|---|---|---|
| 4.0 | 3.8 | 0.70 |
| 5.0 | 6.9 | 0.36 |
| 6.0 | 2.4 | 0.10 |
| 7.0 | 1.3 | 0.10 |

[a]Data obtained with isPNC.

Double reciprocal plots of oxidase activity for various coated nanoceria preparations at pH 4.0 are shown in FIGS. 12A to 12D. A constant concentration of different coated nanoceria preparations are used with TMB as a substrate. The slope of each plot shows that as the hydrodynamic diameter of the nanoparticles increases, lower $K_m$ and $V_{max}$ values are obtained as shown in Table 2 below.

TABLE 2

Comparison of nanoceria's size-dependent kinetic parameters[a]

| Nanoceria | Size (nm) | $K_m$ (mM) | $V_{max}$ (µM/s) |
|---|---|---|---|
| isPNC | 5 | 3.8 | 0.7 |
| isDNC | 14 | 2.1 | 0.6 |
| swPNC | 12 | 1.5 | 0.5 |
| swDNC | 100 | 0.8 | 0.3 |

[a]Data obtained at pH 4.0

Figure 12A:
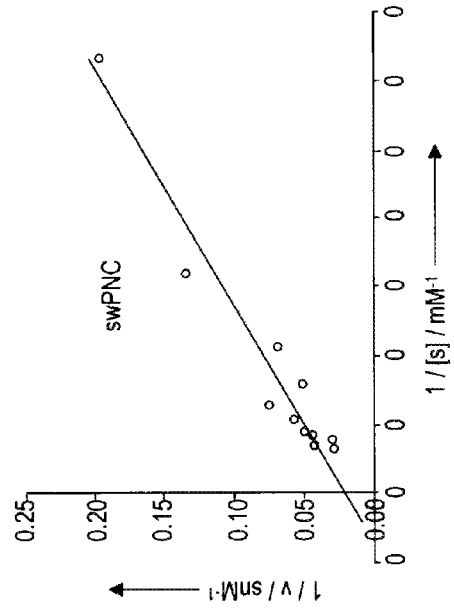
FIG. 12A is a double reciprocal plot of oxidase activity of in-situ synthesized polyacrylic acid coated nanoceria (PNC) at pH 4.0 using 3,3',5,5'-tetramethyl benzidine (TMB) as substrate providing a steady state kinetic assay.
Figure 12B:
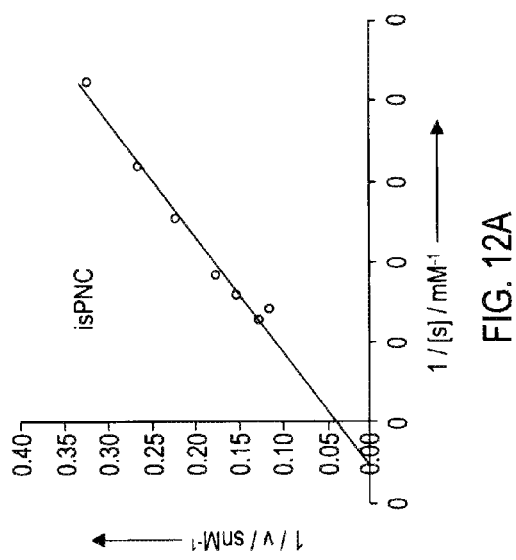
FIG. 12B is a double reciprocal plot of oxidase activity of step-wise synthesized polyacrylic acid coated nanoceria (PNC) at pH 4.0 using 3,3',5,5'-tetramethyl benzidine (TMB) as substrate providing a steady state kinetic assay.
Figure 12C:
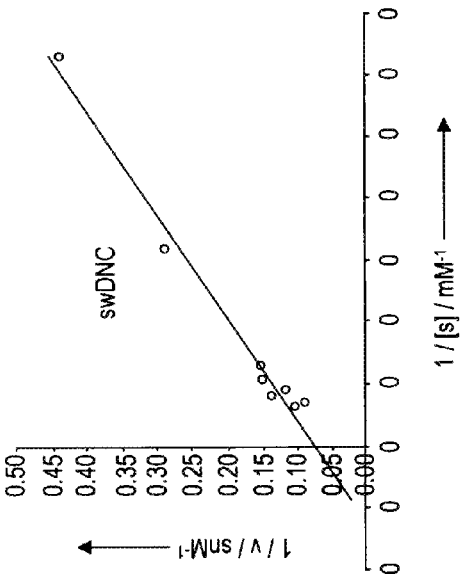
FIG. 12C is a double reciprocal plot of oxidase activity of in-situ synthesized dextran coated nanoceria (DNC) at pH 4.0 using 3,3',5,5'-tetramethyl benzidine (TMB) as substrate providing a steady state kinetic assay.
Figure 12D:
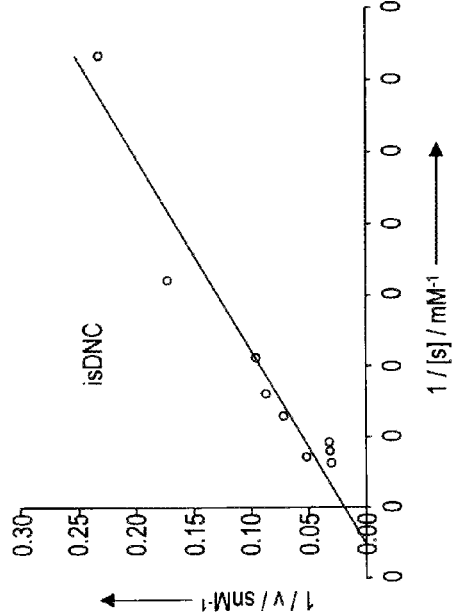
FIG. 12D is a double reciprocal plot of oxidase activity of step-wise synthesized dextran coated nanoceria (DNC) at pH 4.0 using 3,3',5,5'-tetramethyl benzidine (TMB) as substrate providing a steady state kinetic assay.

FIG. 12A shows the steady state kinetic assay of in-situ synthesized polyacrylic acid-coated nanoceria (isPNC). FIG. 12B is a plot of the steady state kinetic of step-wise synthesized PNC (swPNC). FIG. 12C is a plot of the steady state kinetic of in-situ synthesized dextran-coated nanoceria (is-DNC). FIG. 12D is a plot of the steady state kinetic of step-wise synthesized DNC (swDNC). Similar results were observed with AzBTS.

The fact that the nanoceria preparation with the smaller hydrodynamic diameter and thinner coating (isPNC) displays the fastest kinetics, contrary to the swDNC, suggests that the thickness of the polymer coating plays a key role in the rate of oxidation of the substrate.

EXAMPLE 8

Surface-Modified Ceria Used in Immunoassays

Figure 13:
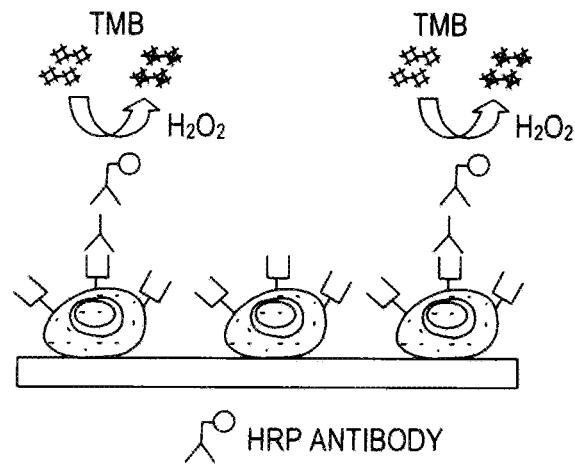
FIG. 13 is a schematic design of traditional Enzyme-Linked ImmunoSorbent Assay (ELISA) with a horseradish peroxidase (HRP) labeled secondary antibody treated with hydrogen peroxide to facilitate oxidation of 3,3',5,5'-tetramethyl benzidine (TMB) resulting in color development (PRIOR ART)

The oxidase activity of nanoceria in slightly acidic aqueous solution makes them potentially useful as aqueous redox catalyst and as aqueous oxidants of water pollutants, according to B. Meunier, Science 2002, 296, 270. An immediate and equally important application of this technology is in the design of more robust and reliable TMB-based immunoassays using surface-modified or coated cerium oxide nanopaiticles. In traditional ELISA, a horseradish peroxidase (HRP) labeled secondary antibody is utilized to assess the binding of a specific primary antibody to a particular target or surface receptor as shown in FIG. 13. This binding event is assessed by the ability of HRP to oxidize a chromogenic substrate such as TMB in the presence of hydrogen peroxide. In traditional ELISA, a high rate of negative results is mainly attributed to (1) the instability of the antibodies that when denatured do not bind effectively to their target, (2) the instability of HRP that when denatured loses its peroxidase activity or (3) the instability of hydrogen peroxide which upon prolonged storage decomposes and losses its ability to oxidize the substrate TMB in the presence of HRP.

Figure 14:
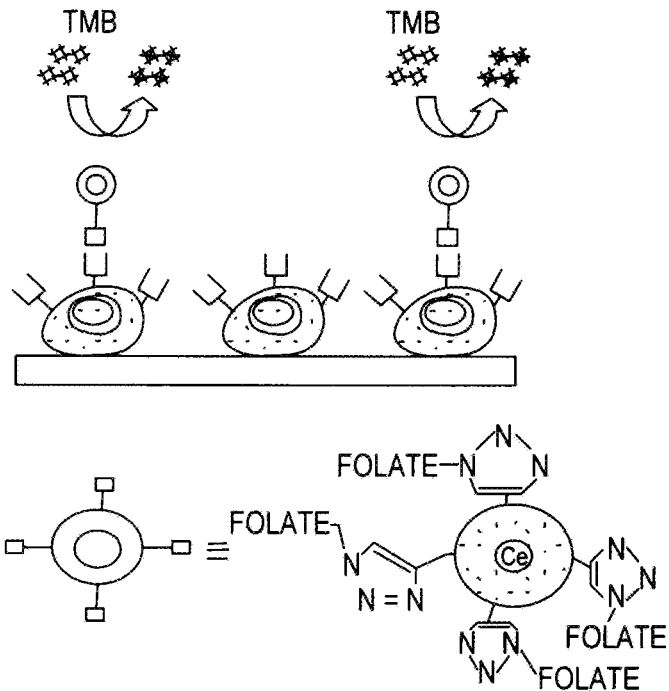
FIG. 14 is a schematic design of a polymer coated nanoceria-based ELISA showing the direct oxidation of 3,3',5,5'-tetramethyl benzidine (TMB) without the use of HRP or hydrogen peroxide.

It was hypothesized and tested that a coated nanoceria-based detection approach is more robust than current HRP-based assays, as no enzyme or hydrogen peroxide would be needed for detection as shown in FIG. 14. The oxidase activity of the coated nanoceria, by itself, can facilitate the oxidation and corresponding color development. In FIG. 14, coated nanoceria is used to directly oxidize 3,3',5,5'-tetramethyl benzidine (TMB) without the use of HRP or hydrogen peroxide. Using this assay, one can perform an immunoassay and identify the presence and concentration of a target faster and more economically.

Coated nanoceria-based assays outperform the traditional sandwich ELISA, which requires hydrogen peroxide and an additional step to introduce an antibody carrying horseradish peroxidase (HRP-antibody) to allow detection. Thus, the nanoceria-based method using the polymer coated nanoceria particles of the present invention is easier, faster, more economical, and provides greater sensitivity.

EXAMPLE 9

Coated Nanoceria Conjugated to Folic Acid as Detection Tool

For this purpose, polyacrylic acid coated nanoceria (isPNC) was conjugated to folic acid using click chemistry, a chemical philosophy introduced by K. Barry Sharpless in 2001, the year he also received the Nobel Prize in Chemistry.

Figure 15:
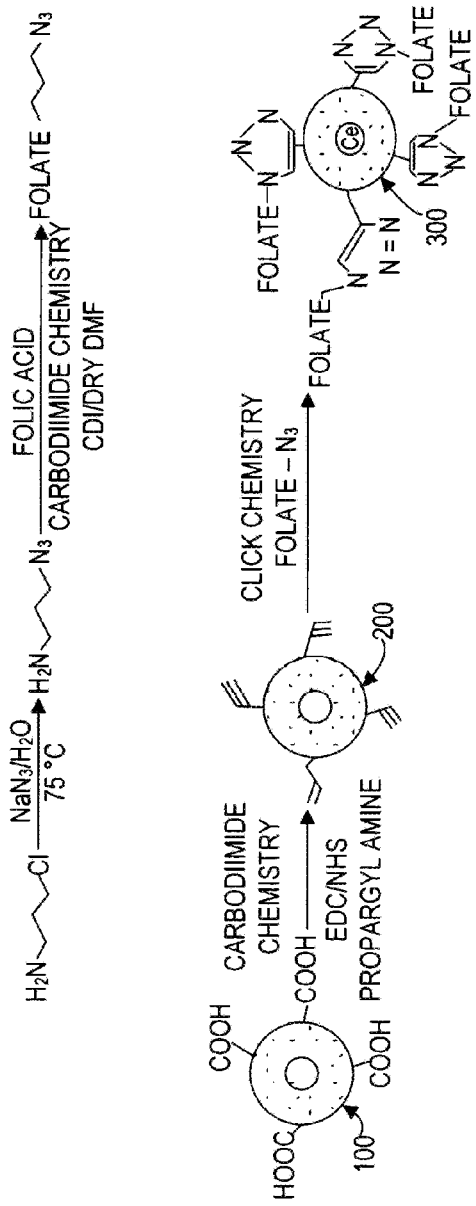
FIG. 15 is a schematic depiction of the synthesis of folate-conjugated nanoceria particles via click chemistry wherein folic acid is used in carbodiimide chemistry to create folate compound that is conjugated to polyacrylic acid (PAA) coated nanoceria.

In FIG. 15, a schematic depiction of the synthesis of a folate-conjugated nanoceria particle is shown for the first time. Folic acid is the ligand for the folate receptor, which is over-expressed in many tumors and cancer cell lines, as reported by H. Yuan et al. in Ira J. Pharm. 2008, 348, 137 and M. E. Nelson et al. in J. Med. Chem. 2004, 47, 3887.

FIG. 15 shows the room temperature synthesis of the folate-conjugated, coated nanoceria particle 300 wherein folic acid is conjugated to polyacrylic acid-coated nanoceria 100 that undergoes triple bond (alkyne) functionalization 200 prior to using click chemistry to form a folate-conjugated nanoceria particle 300.

It was hypothesized that a coated nanoceria conjugate with folic acid instead of an anti-folate receptor antibody will make a more robust nanoprobe for our immunoassay. Moreover, the triple bond (alkyne) functionalized nanoceria 200 in FIG. 15 can facilitate conjugation of an azide derivatized folate ligand via click chemistry, offering the opportunity to conjugate various ligands such as DNA, peptides, proteins, aptamers, other small molecules and the like. This provides proof that coated nanoceria can be conjugated with a small molecule ligand via click chemistry, creating a targetable nanoceria.

Figure 16:
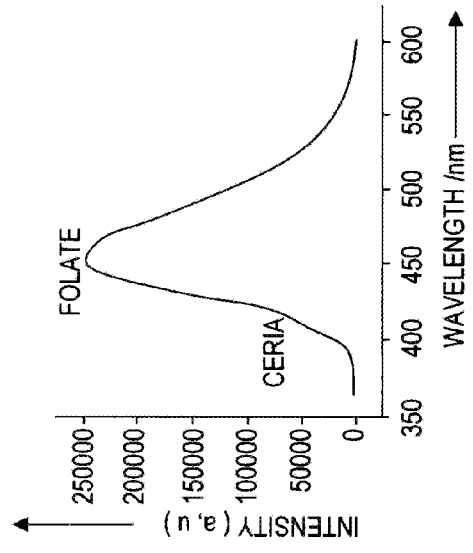
FIG. 16 is the fluorescence profile of folate-conjugated nanoceria particles showing a peak for ceria at 410 nm wavelength and a peak for folate at 450 nm wavelength confirming conjugation was successful using click chemistry.

A fluorescence profile of the folate-conjugated nanoceria particles is shown in FIG. 16 wherein a peak for ceria at 410 nm wavelength and a peak for folate at 450 nm wavelength confirm conjugation was successful using click chemistry.

Experiments were performed using the lung cancer cell line (A-549) which over expresses the folate receptor. In control experiments, cardiac myocytes (H9c2) that do not over express the folate receptor were used. The fact that cardiac myocytes (H9c2) do not over express the folate receptor is reported by N. Parker at al. in Anal. Biochem 2005, 338, 284.

Figure 17:
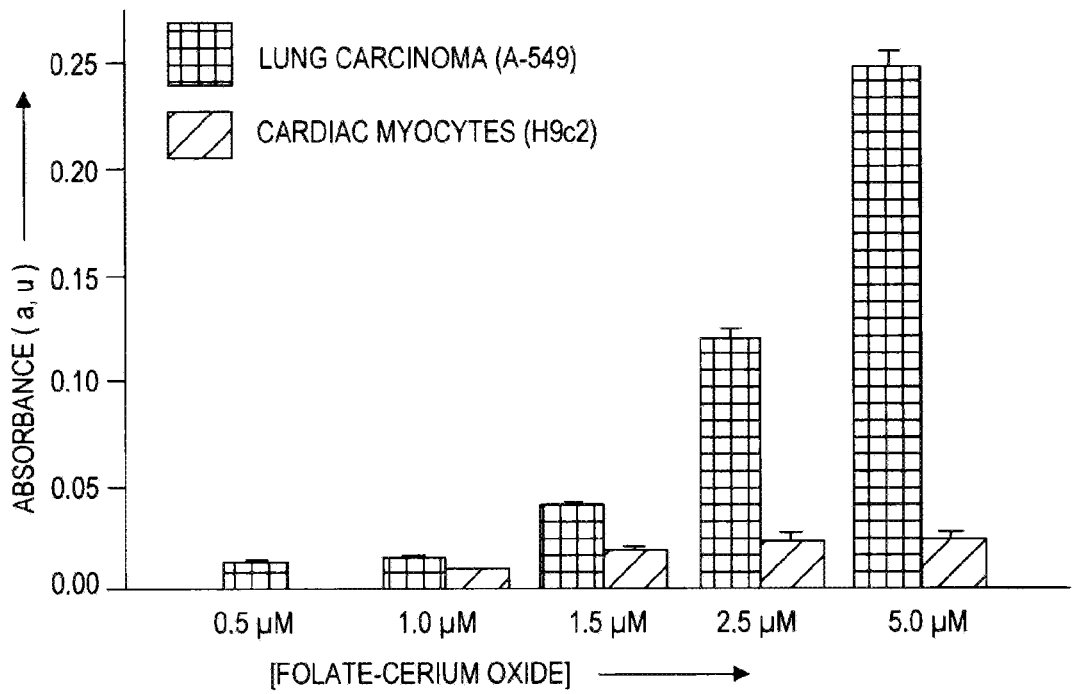
FIG. 17 is a graph of product formation when increasing concentrations (from 0.5 µM -5.0 µM) of folate-conjugated polymer coated nanocaria are incubated separately with lung carcinoma cells (A-549) and cardiac myocytes (H9c2) for three hours followed by incubation with 3,3',5,5'-tetramethyl benzidine (TMB) for 30 minutes at 652 nm wavelength.

In a first set of experiments either A-549 or H9c2 cells (6000 cells) were incubated with increasing amount of folate-cerium oxide nanoparticles in 96-well plate for three hours, followed by incubation with TMB (0.04 mM) for 30 minutes and monitoring of product formation at 652 nm using a microtiter plate reader. As expected, a folate-nanoceria dependent binding was observed for the lung carcinoma cell line (A-549) compared to cardiac myocytes (H9c2) judged by an increase in absorbance at 652 nm with increasing amount of folate-nanoceria as shown in FIG. 17.

Figure 18:
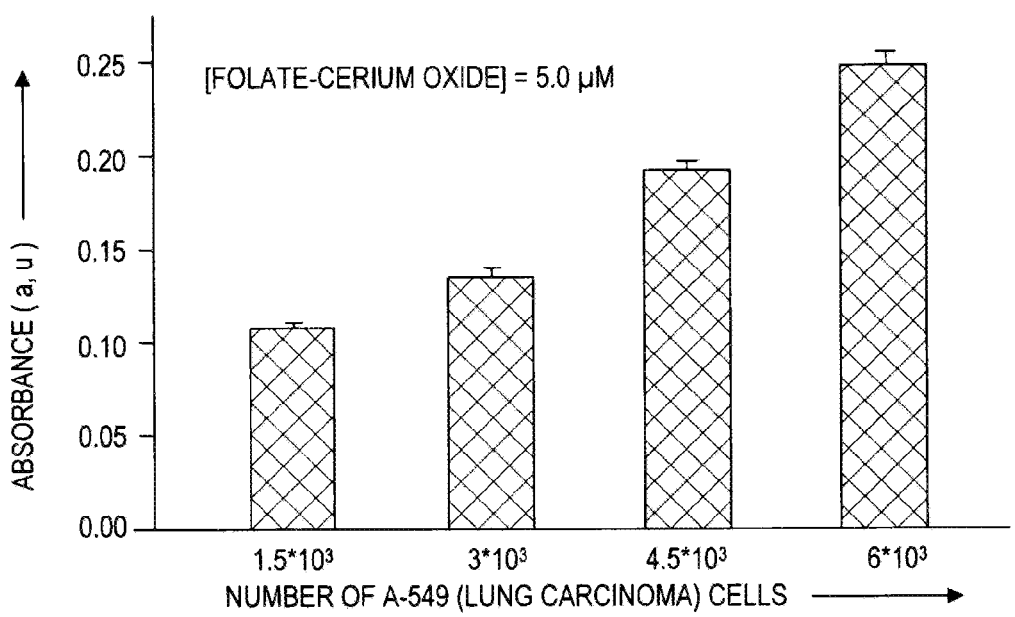
FIG. 18 is a graph showing results when a constant amount (5.0 µM) of folate-conjugated polymer coated nanoceria is exposed to an increasing number (from 1500 to 6000) of folate-positive lung carcinoma cells (A549), the ability of folate-conjugated nanoceria to identify the target carcinoma cells increased as the number of folate receptors increased on lung carcinoma cells.

In a second set of experiments, an increasing number of folate-positive lung carcinoma cells (1500 to 6000 cells) were treated with a constant amount of folate-ceria (5.0 µM). Results show an increase in TMB oxidation product formation (652 nm absorbance) with increasing number of A549 cells as shown in FIG. 18. This was expected as an increasing number of A549 translates into an increasing number of surface folate-receptors available for binding to the folate-nanoceria. These results demonstrate the utility of cerium oxide nanoparticles as a detection tool confirming their dual functionality of binding and detection. Coated nanoceria-based assays outperform the traditional sandwich ELISA, which requires hydrogen peroxide and an additional step to introduce the antibody carrying horseradish peroxidase (HRP) to allow detection. Therefore, the nanoceria-based method is easier, faster, more economical, and provides greater sensitivity.

Prior to the present invention, a facile, cost effective, non-toxic step-wise synthesis of biodegradable polymer coated nanoceria particles was not available. The synthesis does not require surfactants or vigorous experimental conditions and the end-product is suitable for unlimited biomedical, diagnostic and oxidant applications.

The newly developed step-wise synthesis of biodegradable polymer coated ceria nanoparticles presented herein is ideal for tuning oxidase activity based on the thickness of the polymer coating of nanoceria. It was an unexpected finding that a slight change in the synthesis procedure would result in a wide distribution of particle sizes and coating thickness which allow the adjustment of oxidase activity of the coated nanoceria.

Figure 19A:
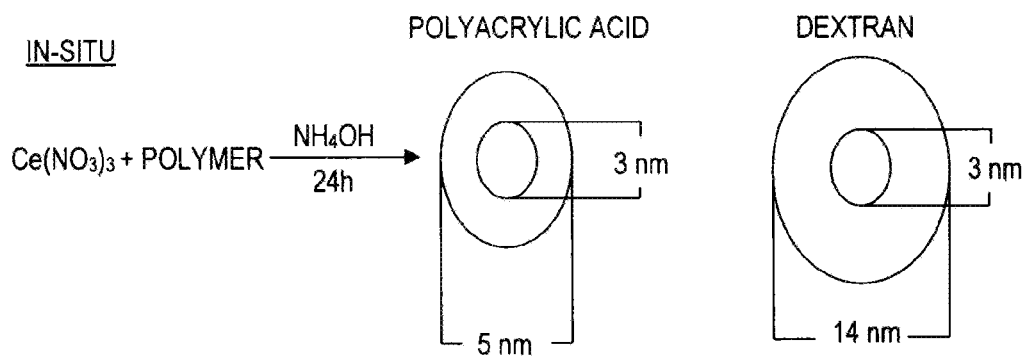
FIG. 19A is a schematic diagram showing the in-situ synthesis of coated nanoceria. In this example, the molecular weight of polyacrylic acid is 1,000 and the molecular weight of dextran is 10,000; a small diameter (3 nm) ceria nanoparticle is coated with a thick polymer coating in the in-situ process.

In FIG. 19A, a schematic representation of in-situ synthesis of polymer coated nanoceria particles shows particles formed in an ammonium hydroxide solution over a 24 hour period. A ceria nanoparticle that is approximately 3 nm in diameter is coated with polyacrylic acid to form a coated particle that is 5am in diameter. A ceria nanoparticle that is approximately 3 nm in diameter is coated with dextran to form a coated particle that is 14 nm in diameter.

Figure 19B:
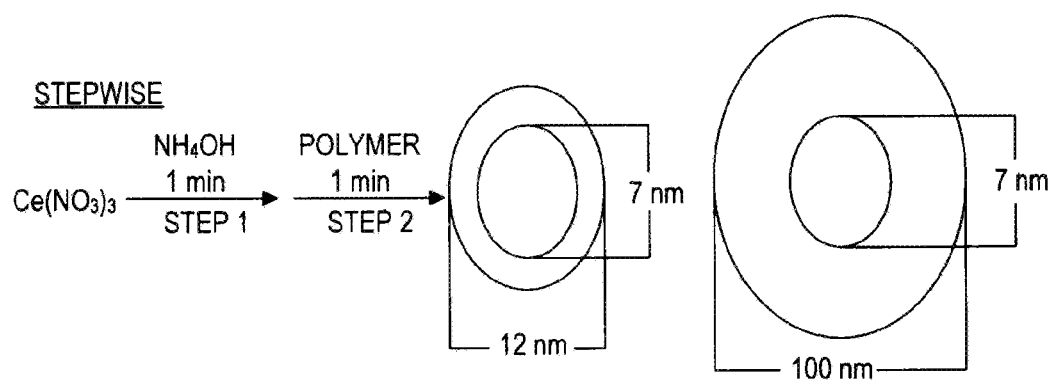
FIG. 19B is a schematic diagram showing the step-wise synthesis of coated nanoceria. In this example, the molecular weight of polyacrylic acid is 1,000 and the molecular weight of dextran is 10,000; a large diameter (7 nm) ceria nanoparticle is coated with a thick polymer in the step-wise process.

FIG. 19B shows that when the ceria nanoparticles are formed in a step-wise synthesis, ceria nanoparticles are formed first and then the polymer is added within minutes and allowed to stand for approximately 3 hours to generate larger ceria nanoparticles in the core of each coated particle and thicker coating on each nanoparticle core. The thickness of polymer coating on nanoceria is a direct result of the synthesis method. The in-situ synthesis method produces a smaller nanoceria core and a thin polymer coating; whereas, the step-wise synthesis method produces a larger nanoceria core and a thicker polymer coating. More specifically, in FIG. 19B, step-wise synthesis produces ceria nanoparticles that are approximately 7 nm in diameter and with a polyacrylic acid coating the coated particle measures 12 nm in diameter, whereas, a dextran coating of a 7 nm ceria nanoparticle results in a coated particle that is approximately 100 nm in diameter. Thickness of coating affects utility.

Oxidase Activity of Ceria Nanoparticles in Acidic to Moderately Alkaline pH

Oxidase activity of polymer-coated cerium oxide nanoparticles in an acidic pH range from approximately 1.0 to approximately 4.0 is demonstrated in the present invention wherein test data show the ability of nanoceria to oxidize various chromogenic/colorimetric dyes such as TMB, AzBTS and an organic molecule dopamine.

It is possible to extend the range of the oxidase activity of polymer coated cerium oxide nanoparticles from approximately 4.0 to a pH value of approximately 8.0. It was a surprising and unexpected discovery that the oxidase activity of nanoceria is dependent not only on the pH but also on the nature of the dye substrate utilized. Some substrates upon oxidation are converted to a fluorescent product and oxidized by nanoceria at both acidic pH and moderately alkaline pH, such as in a range of from approximately 4.0 to approximately 8.0.

Thus, when using chromogenic dye substrates oxidation occurred at acidic pH values between approximately 1.0 and approximately 4.0. When using a chromogenic/fluorescent dye substrate, such as amplilfu (amplex red) and o-phenylene diamine (OPD) oxidation of the fluorescent product using polymer coated cerium oxide nanoparticles occurred at pH ranges between approximately 4.0 and approximately 8.0.

Ampliflu (10-acetyl-3,7-dihydroxyphenoxazine) is used as a sensitive stable substrate for peroxidase detection and is oxidized in the presence of horseradish peroxidase/hydrogen peroxide to fluorescent Resorufin. In contrast, nanoceria is able to oxidize these substrates to fluorescent products at acidic, neutral and moderately alkaline pH values, in the absence of $H_2O_2$.

In addition, polymeric cerium oxide nanoparticles are conjugated to Protein-G using EDC/NHS carbodiimide chemistry. This allowed the conjugation of an antibody to the nanoceria in order to perform antibody based cellular ELISA using a fluorimetric assay. Since fluorimetric assays tend to be more sensitive than chromogenic/colorimetric assays, it is possible to detect, using antibody conjugated nanoceria and ampliflu, down to 500 cancer cells via cellular ELISA.

Figure 20A:
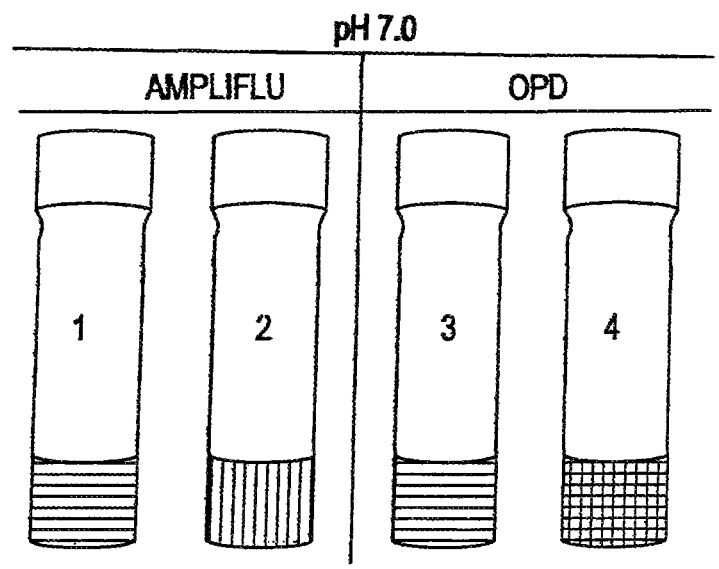
FIG. 20A is a drawing of vials containing polymeric cerium oxide nanoparticles used in the oxidation of colorimetric/fluorimetric dye substrates, Ampliflu and OPD, at pH 7.0.

FIGS. 20A to 20D show that the polymer coated cerium oxide nanoparticles efficiently oxidize Ampliflu and o-phenylene diamine at both pH 7.0 and pH 4.0. Vials 1 and 3 in each figure contain a citrate-buffered solution of coated cerium oxide nanoparticles with a clear color. In FIG. 20A, Ampliflu is added to the clear citrate-buffered solution of coated cerium oxide nanoparticles 1, at pH 7.0, yielding a red color 2. Also, in FIG. 20A, o-phenylene diamine is added to the clear citrate buffered solution of coated cerium oxide nanoparticles 3, at pH 7.0, yielding a yellow color 4.

Figure 20B:
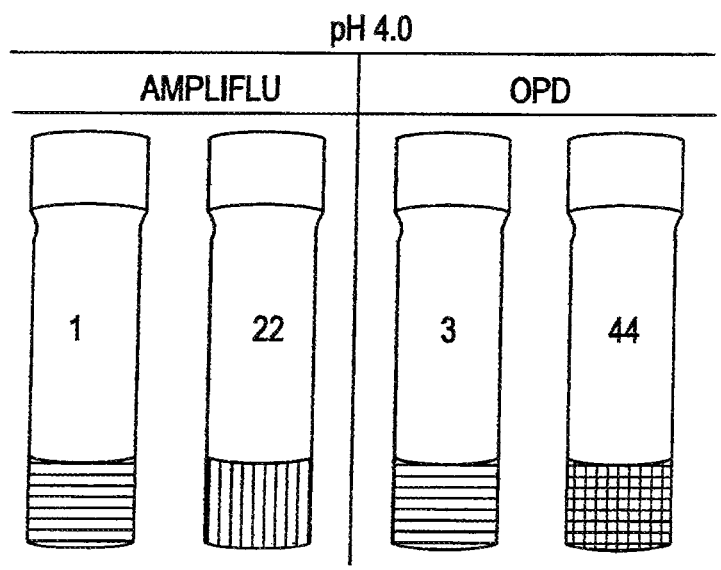
FIG. 20B is a drawing of vials containing polymeric cerium oxide nanoparticles used in the oxidation of colorimetric/fluorimetric dye substrates, Ampliflu and OPD at pH 4.0.

In FIG. 20B, Ampliflu is added to the clear citrate-buffered solution of coated cerium oxide nanoparticles 1, at pH 4.0, yielding a red color 22. Also, in FIG. 20B, o-phenylene diamine is added to the clear citrate buffered solution of coated cerium oxide nanoparticles 3, at pH 4.0, yielding a yellow color 44.

Figure 20C:
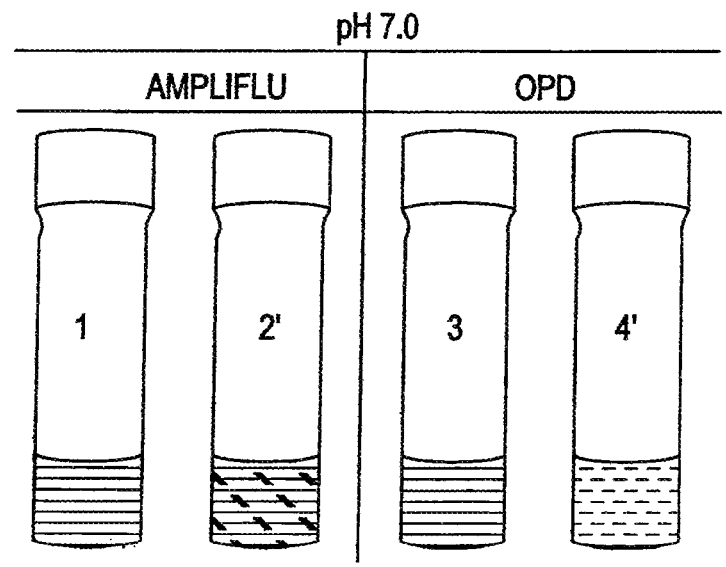
FIG. 20C is a drawing of an ultraviolet (UV) image of vials containing polymeric cerium oxide nanoparticles used in the oxidation of colorimetric/fluorimetric dye substrates, Ampliflu and OPD, at pH 7.0.
Figure 20D:
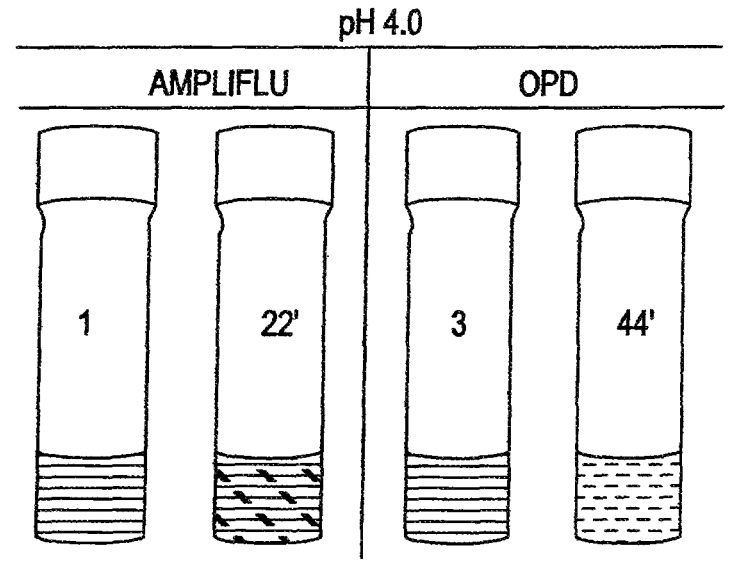
FIG. 20D is a drawing of an ultraviolet (UV) image of vials containing polymeric cerium oxide nanoparticles used in the oxidation of colorimetric/fluorimetric dye substrates, Ampliflu and OPD, at pH 4.0.

FIGS. 20C and 20D provide visual data on the fluorescent properties of the oxidation products obtained on the addition of Ampliflu and o-phenylene diamine to clear citrate-buffered solutions of coated cerium oxide nanoparticles. In FIG. 20C, Ampliflu is added to the clear citrate-buffered solution of coated
cerium oxide nanoparticles 1, at pH 7.0, and the oxidation reaction product under UV light shows bright orange/red fluorescent color 2'. Also, in FIG. 20C, o-phenylene diamine is added to the clear citrate buffered solution of coated cerium oxide nanoparticles 3, at pH 7.0, yielding an oxidation reaction product which under UV light shows a bright yellow fluorescent color 4'.

In FIG. 20D, Ampliflu is added to the clear citrate-buffered solution of coated cerium oxide nanoparticles 1, at pH 4.0, and the oxidation reaction product under UV light shows bright orange/red fluorescent color 22'. Also, in FIG. 20D, o-phenylene diamine (OPD) is added to the clear citrate buffered solution of coated cerium oxide nanoparticles 3, at pH 4.0, yielding an oxidation reaction product which under UV light shows a bright yellow fluorescent color 44'.

Collectively, FIGS. 20A-20D confirm that nanoceria mediated oxidized product of Ampliflu and o-phenylene diamine (OPD) can be used both as colorimetric and fluorimetric substrates especially in ELISA. These oxidations reaction have been carried out in pH range 4.0 to 8.0.

Advantages of using Ampliflu as peroxidase substrate in ELISA is because its fluorescent product has excitation/emission maxima of 570/585, in this range there is much less interference from the auto fluorescence of most biological samples. This property makes Ampliflu a suitable reagent for various immunoassays and cellular ELISA. In addition, by using fluorescence one could get a more sensitive assay.

Figure 21A:
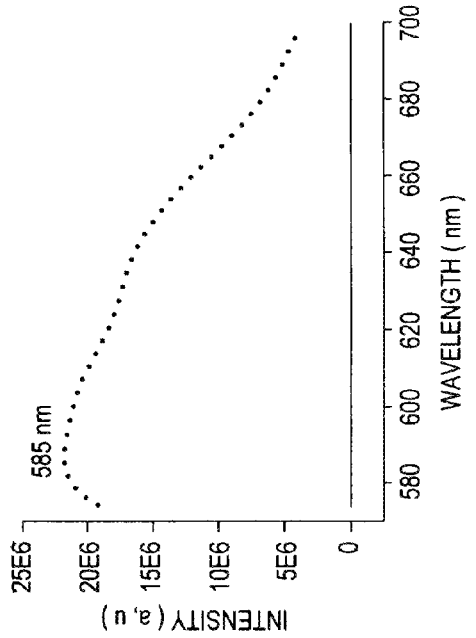
FIG. 21A is a graph of the UV spectrum for oxidized Ampliflu showing the absorbance maximum at 565 nm wavelength.
Figure 21B:
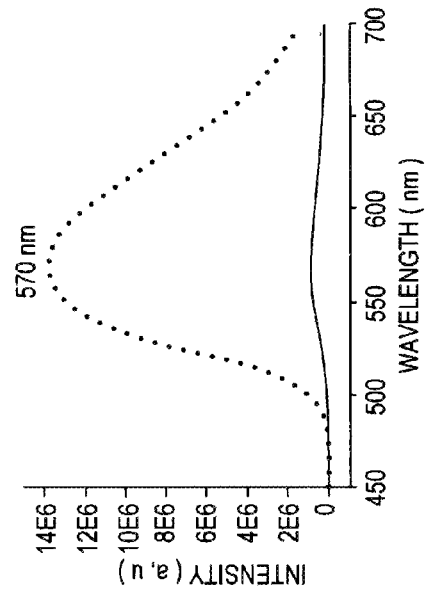
FIG. 21B is a graph of the fluorescence spectrum of oxidized Ampliflu showing an emission peak at 585 nm wavelength.
Figure 21C:
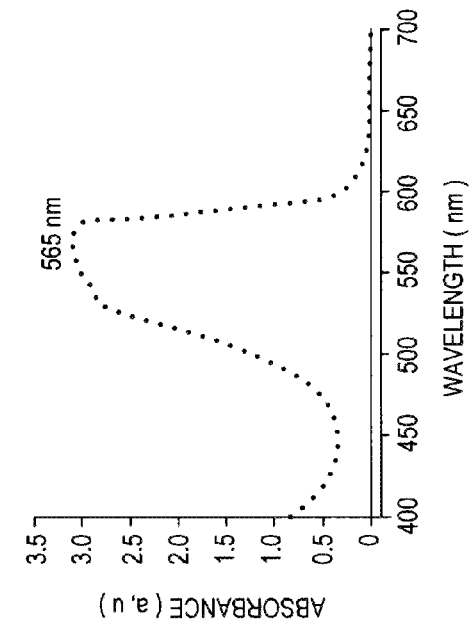
FIG. 21C is a graph of UV spectrum for oxidized o-phenylene diamine showing the absorbance maximum at 417 nm wavelength.

The ultraviolet (UV) profile of oxidized product of Ampliflu is shown in FIG. 21A wherein the absorbance maximum is at 565 nm and the absorbance maximum for o-phenylene diamine is shown at 417 nm in FIG. 21C.

Figure 21D:
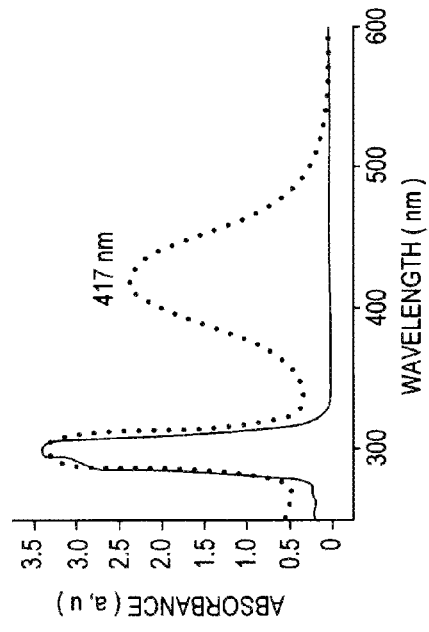
FIG. 21D is a graph of the fluorescence spectrum of oxidized o-phenylene diamine showing an emission peak at 570 nm wavelength.

The fluorescence spectrum for oxidized Ampliflu shows an emission peak at 585 nm in FIG. 21B and an emission peak at 570 nm is shown for oxidized o-phenylene diamine in FIG. 21D. Together, FIGS. 21A and 21C establish identifying profiles for oxidized product of Ampliflu and FIGS. 21B and 21D provide identifying data for oxidized product of o-phenylene diamine (OPD).

Figure 22:
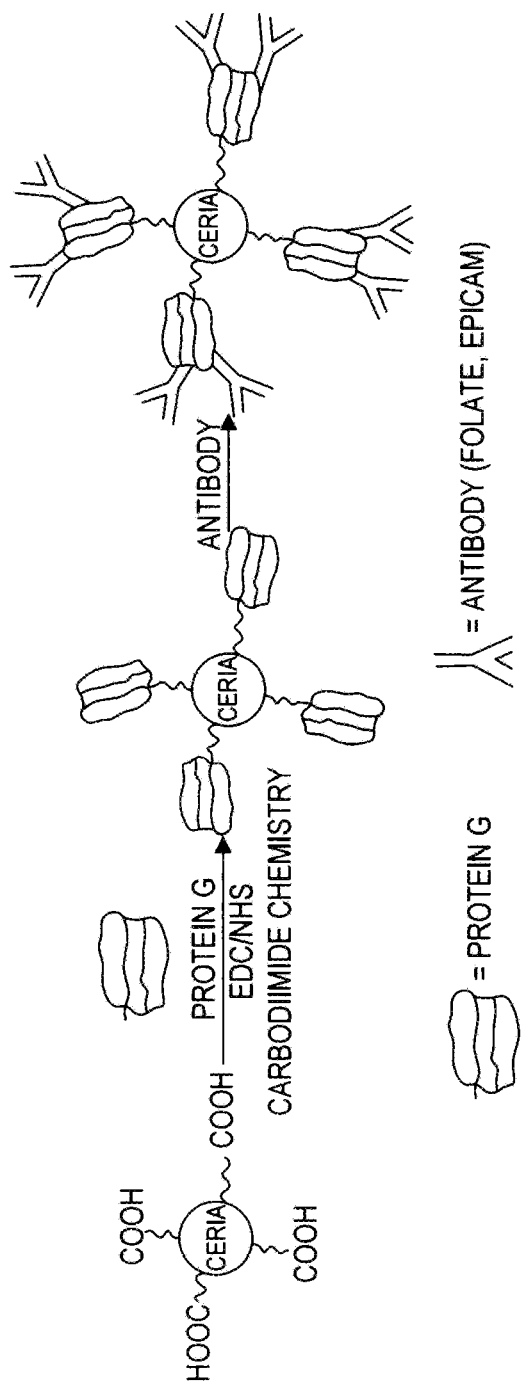
FIG. 22 is a schematic representation of the conjugation of Protein-G on polyacrylic acid coated cerium oxide nanoparticles.

FIG. 22 is a schematic representation of the conjugation of Protein-G on polyacrylic acid coated cerium oxide nanoparticles. Polyacrylic acid coated nanoceria is successfully functionalized with protein-G using carbodiimide chemistry. Protein-G introduces versatility in the system since protein-G can be used to immobilize various antibodies. A similar result is obtainable using Protein-A. This technique allowed us to conjugate various antibody such as antifolate-receptor antibody, EpiCam antibody and the like, depending upon the target.

Figure 23:
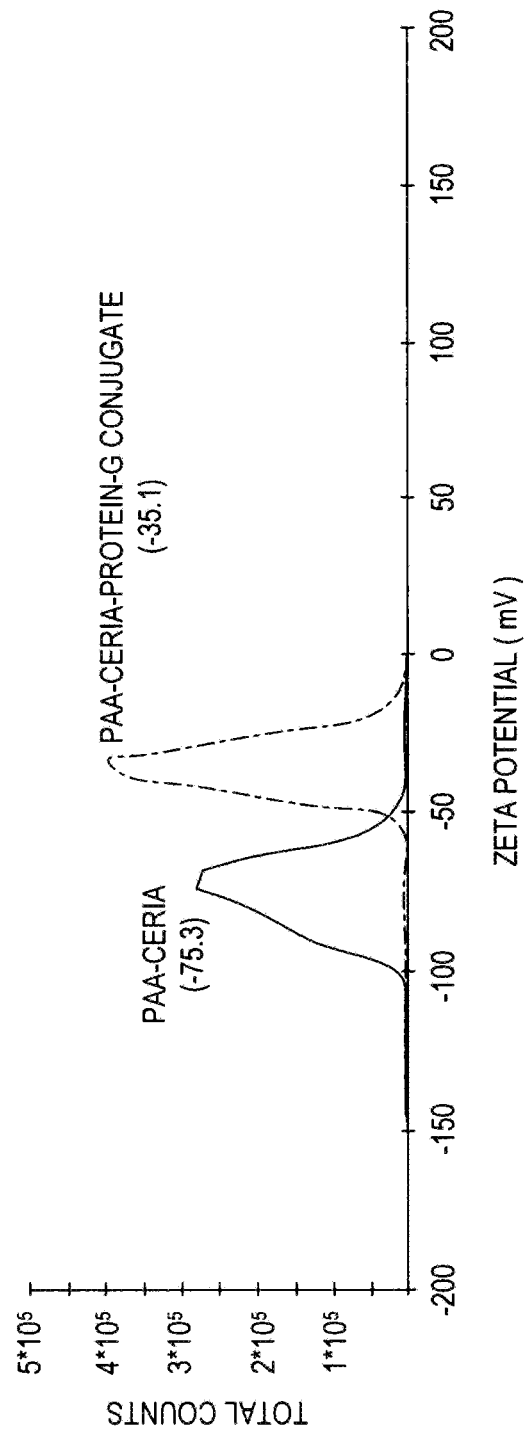
FIG. 23 is a graph confirming the protein-G conjugation to polyacrylic acid coated (PAA-Ceria) nanoceria by zeta potential measurement.

In FIG. 23 the surface conjugation of protein-G on polyacrylic acid coated nanoceria was confirmed by measurement of zeta potential, which shows a shift in zeta potential value from −75.3 for nanoceria to −35.1 mV for conjugated nanoceria.

Figure 24B:
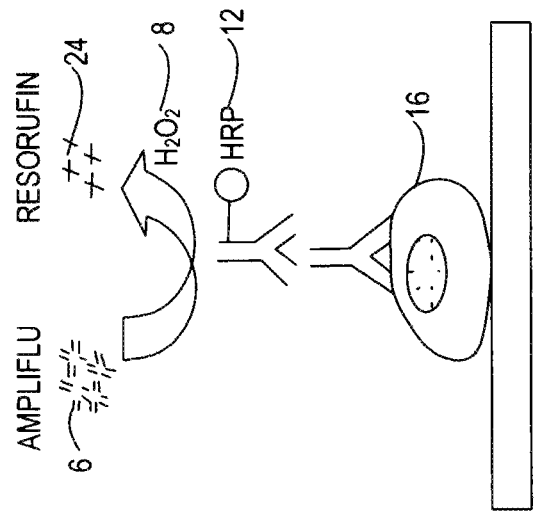
FIG. 24B is a schematic drawing showing traditional state-of-the-art horseradish peroxidase/hydrogen peroxide (HRP/$H_2O_2$) antibody based ELISA. (PRIOR ART)
Figure 24A:
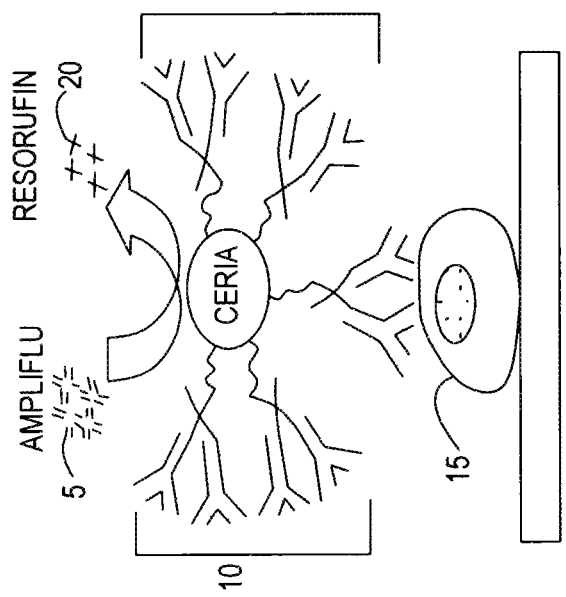
FIG. 24A is a schematic drawing showing nanoceria-Protein-G-antibody based cellular ELISA.

FIG. 24A is a schematic drawing of nanoceria-Protein-G antibody based cellular ELISA with Ampliflu substrate 5 wherein a single nanoparticle conjugate 10 is employed to monitor the expression of surface cell receptor 15 by changing the antibody on nanoparticle conjugate 10 to the oxidized version 20. In FIG. 24B, a traditional cell based ELISA shows the use of Ampliflu substrate 6 with hydrogen peroxide 8 and horseradish peroxidase antibody 12 to monitor the expression of surface cell receptor 16 by changing the antibody on horseradish peroxidase 12 to the oxidized version 24. The advantage of the process in FIG. 24A over the traditional process in FIG. 24B is that the toxic hydrogen peroxide component can be omitted.

FIG. 25A is a graph showing nanoceria-protein-G-antifolate receptor antibody conjugate used to monitor the expression of folate receptor on folate positive lung carcinoma cell line (A-549 cells).

As a control, FIG. 25B is a graph showing that it was not possible to monitor the expression of folate receptor in MCF-7 breast carcinoma cell lines which do not express the folate receptor. As shown by the graph in FIG. 25B, no significant signal intensity was found with MCF-7 cell lines.

Figures 26A, 26B:
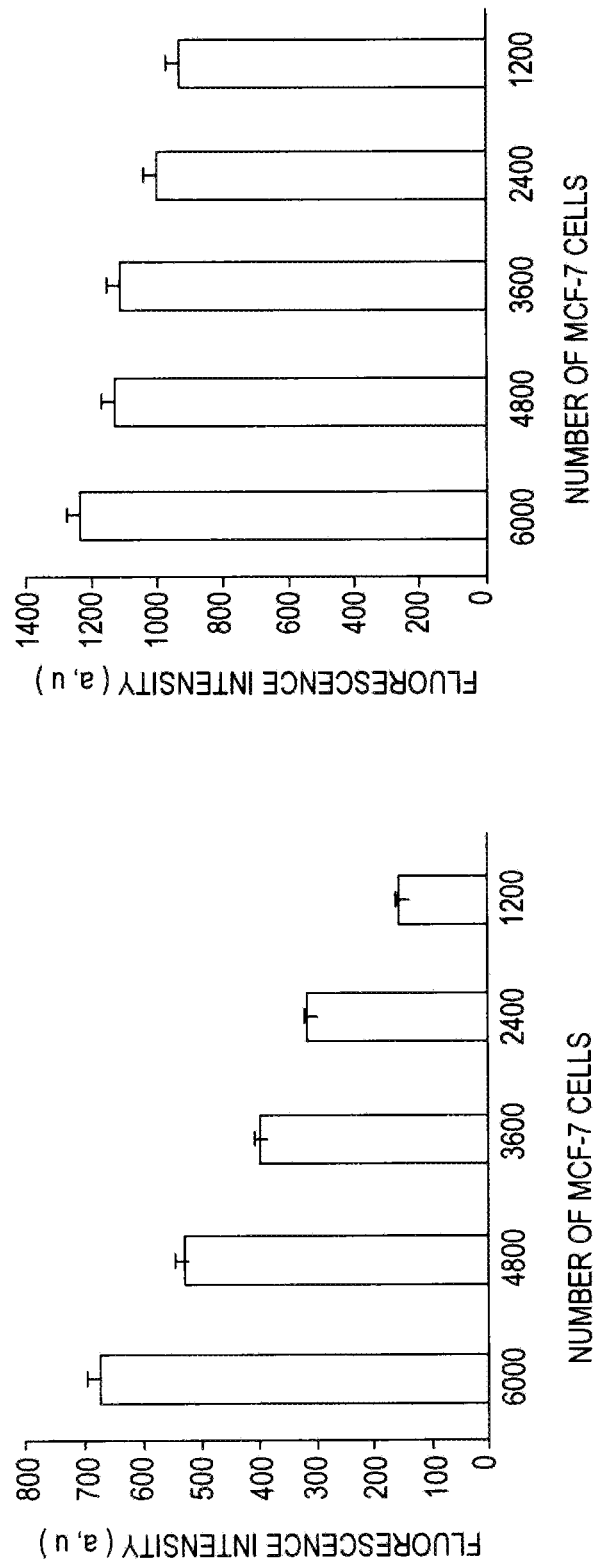
FIG. 26A is a graph showing the expression of Epithelial Cell Adhesion Molecule (Epi-CAM) on MCF-7 breast carcinoma cell lines using nanoceria-Protein-G-conjugated with an anti-Epi-CAM antibody-conjugate.
FIG. 26B is a graph showing the screening of Epi-CAM receptor on MCF-7 breast carcinoma cell lines using the traditional horseradish peroxidase/hydrogen peroxide (HRP/$H_2O_2$) system.

FIG. 26A is a graph showing the expression of Epi-CAM on MCF-7 cell lines using a nanoceria-Protein-G-antiEpi-CAM antibody-conjugate. FIG. 26B is a graph showing the expression of the Epi-CAM on MCF-7 cell lines using the traditional HRP/$H_2O_2$ system. A comparison of the graphs reveals that in FIG. 26A the nanoceria conjugate provides a better cell density curve and gives better signal intensity differences based on the number of cells being screened. In FIG. 26B, when screening the same number of cells, due to saturation, the HRP/$H_2O_2$ system can not provide a clear distinction or signal intensity based at different numbers of cells or saturation levels. Thus, the nanoceria conjugate of the present invention provides greater sensitivity when screening for presence of cancer cells using fluorimetric methods.

Figure 27B:
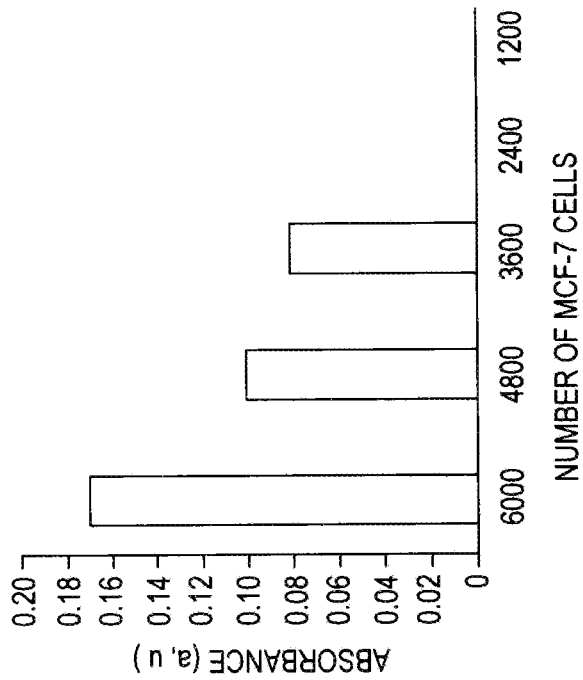
FIG. 27B is a graph of the absorbance of chromogenic substrate to detect MCF-7 breast carcinoma cells at pH 4.0
Figure 27A:
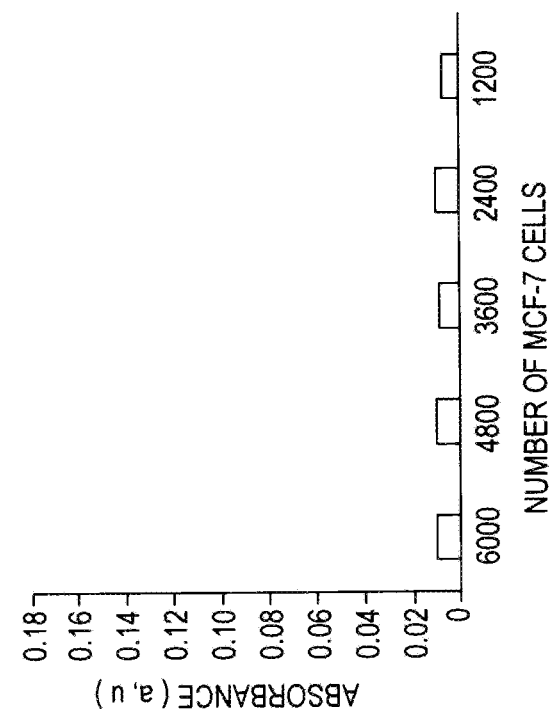
FIG. 27A is a graph of the absorbance of a fluorescent chromogenic substrate to detect MCF-7 breast carcinoma cells at pH 7.0

FIG. 27A and FIG. 27B provide a graphic view of the disadvantages of using a colorimetric substrate, such as TMB, in the nanoceria mediated detection of Epi-CAM in MCF-7 cells.

In FIG. 27A, at ph 7.0 and with chromogenic cellular ELISA using TMB (a colorimetric substrate) it was not possible to obtain enough signal intensity to detect the Epi-CAM expression MCF-7 cells. This is due to the fact that nanoceria cannot oxidize at pH 7 the colorimetric dye TMB. In FIG. 27B, at pH 4.0 using cellular ELISA and colorimetric substrate TMB, the colorimetric cellular ELISA with TMB has detection limit up to 3600 cells employing nanoceria-protein-G-epicam antibody conjugate. Thus, at pH 4, nanoceria can indeed oxidize the colorimetric substrate (TMB) and achieve detection of Epi-CAM expressing cells, although not as good as with a fluorescent dye (such as ampiflu or OPD).

An additional advantage of using Ampliflu is in cyclic oxidation of Ampliflu using nanoceria as measured by XPS. The data confirms that nanoceria indeed possesses an enzymatic auto regenerative behavior toward the oxidation of Ampiflu resulting in a sensitivity and detection limit that can be regenerated rather than continued replacement of reagents.

Figure 28A:
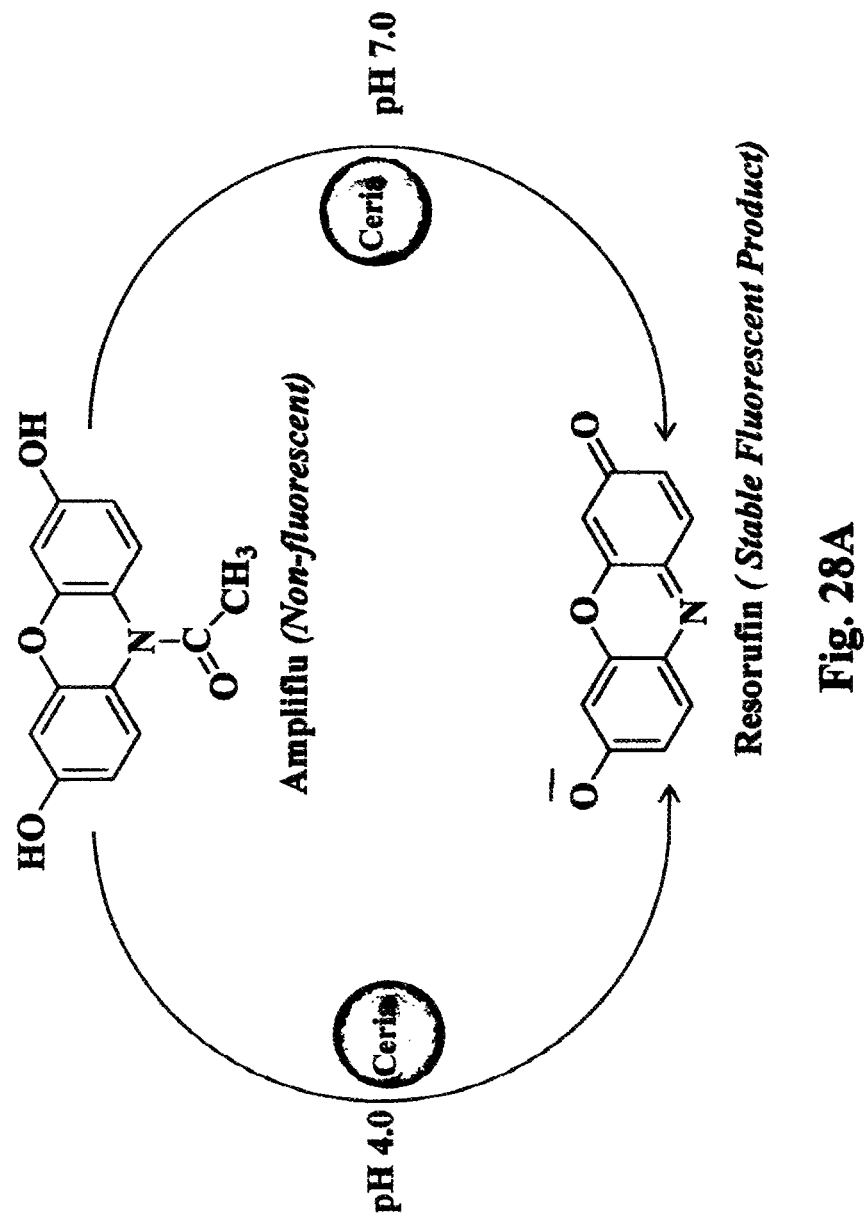
FIG. 28A is a schematic drawing of nanoceria mediated oxidation of Ampliflu to produce a stable fluorescent product
Figure 28B:
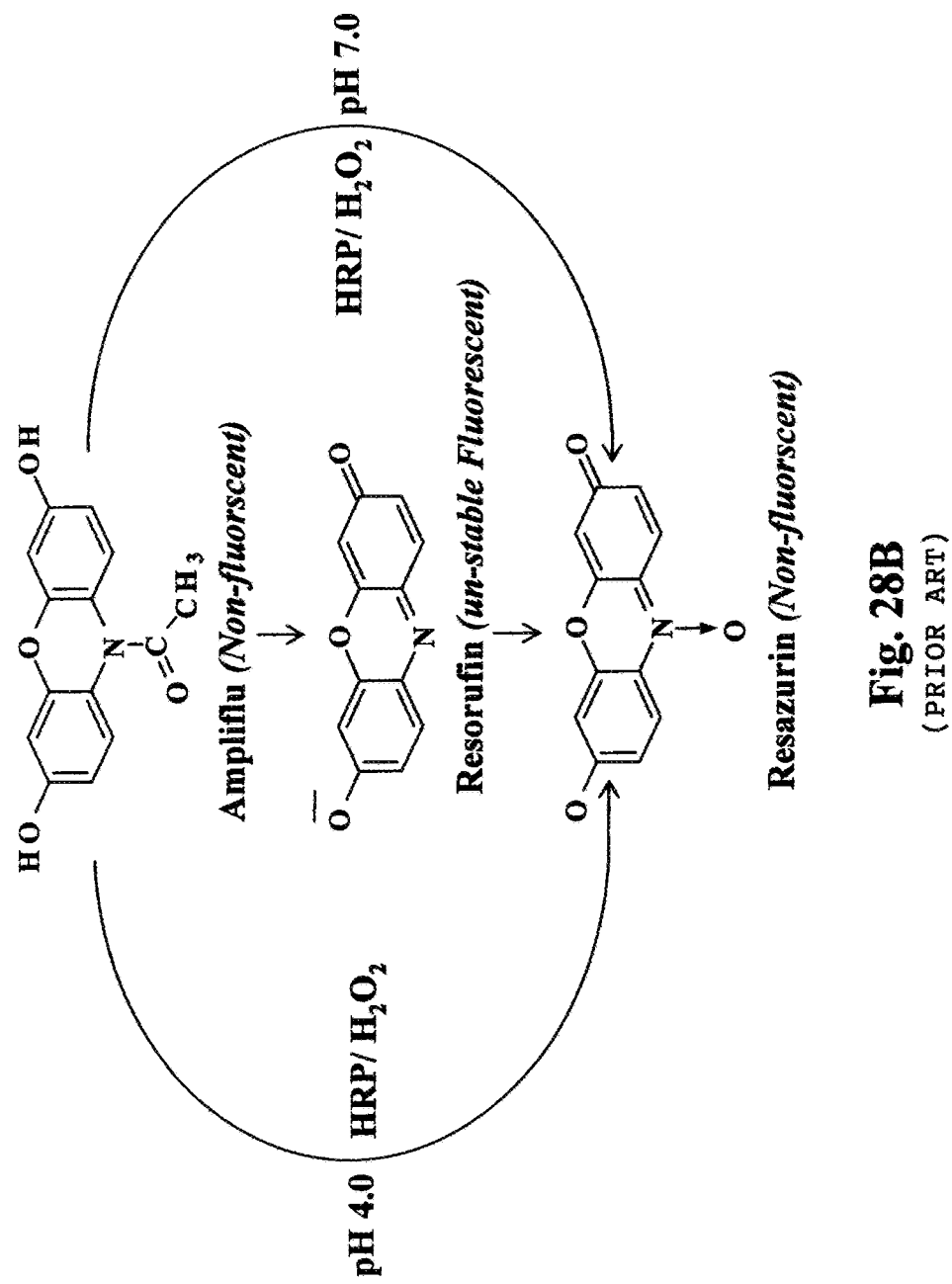
FIG. 28B is a schematic drawing of traditional, state-of-the-art horseradish peroxidase/hydrogen peroxide (HRP/$H_2O_2$) mediated oxidation of Ampliflu that produces an unstable fluorescent product that becomes a non-fluorescent final product. (PRIOR ART)

FIGS. 28A and 28B are schematic representations that compare the mediated oxidation of Ampliflu by nanoceria and traditional HRP/$H_2O_2$. In FIG. 28A, at pH 4.0 or pH 7.0, a robust nanoceria particle system, without hydrogen peroxide, provides only one final, stable fluorescent oxidation product. In FIG. 28B, at pH 4.0 and pH 7.0, HRP/$H_2O_2$ mediated oxidation is labile to concentration of HRP, $H_2O_2$ and experimental conditions, resulting in non-fluorescent oxidation product, which may hamper the ELISA. Thus, it has been determined that the nanoceria mediated oxidation of Ampliflu is preferable to HRP/$H_2O_2$ mediated oxidation of Ampliflu.

In Table I below, the advantages of nanoceria based oxidation of peroxidase substrate and cellular ELISA are summarized, and are not a limitation to the invention.

| Advantages of Nanoceria's Oxidase like behavior | | | |
|---|---|---|---|
| Reagents | Abs* | Ent* | Advantages |
| Ampliflu | 570 | 585 | Fast fluorescence and color development |
| | | | Gives stable fluorescent product resorufin |
| | | | Single reagent based and more sensitive |
| | | | Independent of HRP/$H_2O_2$ |
| o-phenylene diamine (OPD) | 417 | 570 | Fast fluorescence and color development |
| | | | Gives stable fluorescent product |
| | | | Independent of HRP/$H_2O_2$ |
| | | | Single reagent based |
| TMB[Ref] | 652 | NA | Readily oxidize and fast color development |
| | | | Better kinetic compare to HRP/$H_2O_2$ |
| | | | Independent of HRP/$H_2O_2$ |
| | | | Single reagent based |
| AzBTS[Ref] | 405 | NA | Fast color development |
| | | | Better kinetic compare to HRP/$H_2O_2$ |
| | | | Independent of HRP/$H_2O_2$ |
| | | | Single reagent based |

*Absorbance (Abs) and Emission (Em) maxima in nm.
NA = not applicable

Prior to the present invention, it was not known that coated nanoceria is useful as an aqueous redox catalyst, an aqueous oxidizing agent or oxidase with enhanced activity at pH values between approximately 1 and approximately 8.

Prior to the present invention, it was not known that coated nanoceria is useful in the decomposition, decontamination or inactivation by oxidation of organic contaminants, or pesticides, nerve agents and chemical warfare agents, at acidic pH values between approximately 1 and approximately 8.

Prior to the present invention, it was not known that coated nanoceria is useful as a targetable nanocatalyst, by conjugation or attachment of various targeting ligands to the coating on the nanoparticle; it was also not known that a targetable coated nanoceria is useful as a colorimetric probe in immunoassays, such as ELISA, and other molecule binding assays that involve the use of a molecule in solution that upon oxidation change the color of the solution.

Prior to the present invention, it was not known that a targetable coated nanoceria is useful as a colorimetric probe in histology, where the localization of nanoceria to a particular organ or tissue is assessed by treatment with 3,3',5,5'-tetramethyl benzidine (TMB) or any other oxidation sensitive dye.

In conclusion, we report that coated nanoceria possess unique oxidase activity as it can facilitate the fast oxidation of organic dyes and small molecules in acidic to moderately alkaline conditions measured in a range from pH 1.0 to pH 8.0 without the need of hydrogen peroxide. When compared to other systems that require peroxides or proteins (such as oxidases and peroxidases), coated nanoceria of the present invention is a more robust and economical water-soluble redox nanocatalyst, as it is not susceptible to denaturation or decomposition. Furthermore, conjugation with targeting ligands makes coated nanoceria an effective nanocatalyst and detection tool in immunoassays. Taken together, these results demonstrate that this unique aqueous oxidase activity of coated nanoceria can be used in a wide range of new potential applications in biotechnology, environmental chemistry and medicine.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. Polymer coated cerium oxide nanoparticles, each comprising a cerium oxide core with an average hydrodynamic diameter of approximately 7 nm, and a polymer coating with a thickness to an extent such that said polymer coated cerium oxide nanoparticles have an average hydrodynamic diameter in a range from approximately 12 nm to approximately 100 nm, wherein oxidant property of the polymer coated cerium oxide nanoparticles varies with the thickness of the polymer coating of the polymer coated cerium oxide nanoparticles, and is pH dependent.

2. The polymer coated cerium oxide nanoparticles of claim 1, wherein the oxidant property of the polymer coated cerium oxide nanoparticles decreases with an increase in the thickness of the polymer coating of the polymer coated cerium oxide nanoparticles.

3. The polymer coated cerium oxide nanoparticles of claim 1, wherein said polymer coated cerium oxide nanoparticles are formed by mixing a biocompatible polymer with an aqueous reaction mixture of a cerium salt and ammonium hydroxide after an initial formation of cerium oxide nanoparticles in the reaction mixture, thereby obtaining said average hydrodynamic diameters of the cerium oxide core and the polymer coated nanoparticles.

4. The polymer coated cerium oxide nanoparticles of claim 1, wherein the biocompatible polymer is at least one selected from the group consisting of carbohydrate polymer, synthetic polyol, carboxylated polymer, and derivatives thereof.

5. The polymer coated cerium oxide nanoparticles of claim 4, wherein the carboxylated polymer is polyacrylic acid.

6. The polymer coated cerium oxide nanoparticles of claim 5, wherein the polysaccharide is dextran.

7. The polymer coated cerium oxide nanoparticles of claim 4, wherein the carbohydrate polymer is a polysaccharide.

8. The polymer coated cerium oxide nanoparticles of claim 4, wherein the carbohydrate polymer is reduced dextran, carboxyl methyl reduced dextran, arabinogalactan, or chitosan.

9. The polymer coated cerium oxide nanoparticles of claim 1, wherein the polymer coated cerium oxide nanoparticles exhibit oxidant property in an acidic condition with pH between approximately 1 and approximately 4.

10. The polymer coated cerium oxide nanoparticles of claim 1, wherein the polymer coated cerium oxide nanoparticles are polyacrylic acid-coated cerium oxide nanoparticles having the average hydrodynamic diameter approximately 12 nm.

11. The polymer coated cerium oxide nanoparticles of claim 1, wherein the polymer coated cerium oxide nanoparticles are dextran-coated cerium oxide nanoparticles having the average hydrodynamic diameter approximately 100 nm.

12. The polymer coated cerium oxide nanoparticles of claim 1, wherein the polymer coated cerium oxide nanoparticles further comprise a ligand conjugated to the polymer coating.

13. The polymer coated cerium oxide nanoparticles of claim 12, wherein the ligand is folic acid and the polymer coated cerium oxide nanoparticles are folate-conjugated.

14. The polymer coated cerium oxide nanoparticles of claim 12, wherein the polymer coated cerium oxide nanoparticles having a conjugated ligand bind specifically to a target of an immunoassay and also oxidize a dye for detection in the immunoassay.

15. The polymer coated cerium oxide nanoparticles of claim 1, wherein the polymer coated cerium oxide nanoparticles further comprise an antibody conjugated to the polymer coating.

16. The polymer coated cerium oxide nanoparticles of claim 15, wherein the polymer coated cerium oxide nanoparticles having a conjugated antibody enable detection of a target in a horseradish peroxidase based immunoassay in the absence of the horseradish peroxidase and hydrogen peroxide.

17. The polymer coated cerium oxide nanoparticles of claim 1, wherein the polymer coated cerium oxide nanoparticles are a redox catalyst with an enhanced activity at an acidic pH between approximately 1 and approximately 4.

18. The polymer coated cerium oxide nanoparticles of claim 1, wherein the polymer coated cerium oxide nanoparticles are an oxidizing agent in decomposition, decontamination and inactivation of organic contaminants, pesticides, nerve agents or chemical warfare agents at an acidic pH between approximately 1 and approximately 4.

19. The polymer coated cerium oxide nanoparticles of claim 1, wherein at an acidic pH between approximately 1 and approximately 4 the biocompatible polymer coated cerium oxide nanoparticles are an oxidant to chromogenic dyes, fluorescent dyes, and photoluminescent dyes used for peroxidase or oxidase detection, and enable to oxidize the dyes to cause a color change.

20. The polymer coated cerium oxide nanoparticles of claim 19, wherein said dyes comprise 3,3',5,5'-tetramethyl benzidine (TMB) or 2,2-azinobis-(3-ethylbenzothizoline-6-sulfonic acid) (AzBTS).

21. A reagent for use in biochemical analysis and detection comprising a plurality of polymer coated cerium oxide nanoparticles, each thereof comprising a cerium oxide core with an average hydrodynamic diameter of approximately 7 nm, and a polymer coating with a thickness to an extent such that said polymer coated cerium oxide nanoparticles have an average hydrodynamic diameter in a range from approximately 12 nm to approximately 100 nm, wherein oxidant property of the polymer coated cerium oxide nanoparticles varies with the thickness of the polymer coating of the polymer coated cerium oxide nanoparticles, and is pH dependent.

22. The diagnostic device reagent of claim 21, wherein the oxidant property of the polymer coated cerium oxide nanoparticles decreases with an increase in the thickness of the polymer coating of the polymer coated cerium oxide nanoparticles.

23. The reagent of claim 21, wherein said polymer coated cerium oxide nanoparticles are formed by mixing a biocompatible polymer with an aqueous reaction mixture of a cerium salt and ammonium hydroxide after an initial formation of cerium oxide nanoparticles in the reaction mixture, thereby obtaining said average hydrodynamic diameters of the cerium oxide core and the polymer coated nanoparticles.

24. The reagent of claim 21, wherein the biocompatible polymer is at least one selected from the group consisting of carbohydrate polymer, synthetic polyol, carboxylated polymer, and derivatives thereof.

25. The reagent of claim 24, wherein the carboxylated polymer is polyacrylic acid.

26. The reagent of claim 24, wherein the carbohydrate polymer is a polysaccharide.

27. The reagent of claim 26, wherein the polysaccharide is dextran.

28. The reagent of claim 24, wherein the carbohydrate polymer is reduced dextran, carboxyl methyl reduced dextran, arabinogalactan, or chitosan.

29. The reagent of claim 21, wherein the polymer coated cerium oxide nanoparticles are polyacrylic acid-coated cerium oxide nanoparticles having the average hydrodynamic diameter approximately 12 nm.

30. The reagent of claim 21, wherein the polymer coated cerium oxide nanoparticles are dextran-coated cerium oxide nanoparticles having the average hydrodynamic diameter approximately 100 nm.

31. The reagent of claim 21, wherein the polymer coated cerium oxide nanoparticles further comprise a ligand conjugated to the polymer coating.

32. The reagent of claim 31, wherein the polymer coated cerium oxide nanoparticles having a conjugated ligand bind specifically to a target of an immunoassay and also oxidize a dye for detection in the immunoassay.

33. The reagent of claim 21, wherein the ligand is folic acid and the polymer coated cerium oxide nanoparticles are folate-conjugated.

34. The reagent of claim 21, wherein folate-conjugated polymer coated cerium oxide nanoparticles are specific to folate receptors of cells.

35. The reagent of claim 21, wherein the polymer coated cerium oxide nanoparticles further comprise an antibody conjugated to the polymer coating.

36. The reagent of claim 35, wherein the polymer coated cerium oxide nanoparticles having a conjugated antibody enable detection of a target in a horseradish peroxidase based immunoassay in the absence of the horseradish peroxidase and hydrogen peroxide.

37. The reagent of claim 21, wherein at an acidic pH between approximately 1 and approximately 4 the biocompatible polymer coated cerium oxide nanoparticles are an oxidant to chromogenic dyes, fluorescent dyes, and photoluminescent dyes used for peroxidase or oxidase detection, and enable to oxidize the dyes to cause a color change.

38. The reagent of claim 37, wherein said dyes comprise 3,3',5,5'-tetramethyl benzidine (TMB) or 2,2-azinobis-(3-ethylbenzothizoline-6-sulfonic acid) (AzBTS).

* * * * *